United States Patent
Rothenwaender et al.

(10) Patent No.: US 10,575,923 B2
(45) Date of Patent: Mar. 3, 2020

(54) DRIVE DEVICE FOR A MEDICAL, DENTAL OR SURGICAL TOOL

(71) Applicant: W&H Dentalwerk Bürmoos GmbH, Bürmoos (AT)

(72) Inventors: Michael Rothenwaender, Lamprechtshausen (AT); Hermann Rehrl, Lamprechtshausen (AT); Josef Spitzauer, Oberndorf (AT); Karlheinz Eder, Michaelbeuern (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 449 days.

(21) Appl. No.: 14/944,041

(22) Filed: Nov. 17, 2015

(65) Prior Publication Data
US 2016/0067011 A1    Mar. 10, 2016

Related U.S. Application Data

(63) Continuation of application No. PCT/EP2014/060397, filed on May 21, 2014.

(30) Foreign Application Priority Data

May 22, 2013 (EP) .................... 13168650
May 22, 2013 (EP) .................... 13168704
(Continued)

(51) Int. Cl.
*A61C 1/18* (2006.01)
*A61C 1/14* (2006.01)
(Continued)

(52) U.S. Cl.
CPC .......... *A61C 1/185* (2013.01); *A61B 17/1631* (2013.01); *A61C 1/12* (2013.01); *A61C 1/148* (2013.01)

(58) Field of Classification Search
CPC .......... A61C 1/185; A61C 1/12; A61C 1/148; A61C 1/186; A61C 1/141; F16H 19/001; A61B 17/1631
See application file for complete search history.

(56) References Cited

U.S. PATENT DOCUMENTS 4,371,341 A    2/1983   Nakanishi
6,106,290 A *  8/2000   Weissman ............ A61C 1/148
                                              433/118
(Continued)

FOREIGN PATENT DOCUMENTS

EP    1 078 606    2/2001
FR    779 517      4/1935
(Continued)

*Primary Examiner* — Yogesh P Patel
(74) *Attorney, Agent, or Firm* — Klarquist Sparkman, LLP

(57) ABSTRACT

Different mechanical drive devices for a medical, dental or surgical tool are described that are designed to put the tool into an oscillating, rotational motion, wherein the oscillating, rotational motion comprises an alternating rotation of the tool by a first angle of rotation in a first rotational direction and by a second angle of rotation in a second rotational direction substantially opposed to the first rotational direction, wherein the first and second angles of rotation may have different values, so that during multiple sequential rotations in the first and second rotational directions, the tool cumulatively experiences a rotational motion in a preferred direction.

20 Claims, 11 Drawing Sheets

(30) Foreign Application Priority Data

Jun. 12, 2013 (EP) .................................... 13171613
Apr. 18, 2014 (EP) .................................... 14165294

(51) Int. Cl.
*A61B 17/16* (2006.01)
*A61C 1/12* (2006.01)

(56) References Cited

U.S. PATENT DOCUMENTS

| | | | | |
|---|---|---|---|---|
| 6,293,795 B1 * | 9/2001 | Johnson | ............... | A61C 1/0015 |
| | | | | 433/102 |
| 9,017,076 B2 * | 4/2015 | Danger | ................... | A61C 5/40 |
| | | | | 433/224 |
| 9,844,418 B2 * | 12/2017 | Ramos | ................... | A61C 1/003 |
| 2006/0254007 A1 * | 11/2006 | Banning | ............ | A61C 17/3436 |
| | | | | 15/28 |
| 2010/0268235 A1 | 10/2010 | Teichmann | | |
| 2012/0291294 A1 * | 11/2012 | Middleton | ............... | B26B 7/00 |
| | | | | 30/277.4 |
| 2014/0318287 A1 * | 10/2014 | Eder | ...................... | F16H 19/08 |
| | | | | 74/88 |

FOREIGN PATENT DOCUMENTS

| | | |
|---|---|---|
| FR | 1 397 366 | 4/1965 |
| JP | S56-16410 | 2/1981 |
| JP | H1-107312 | 7/1989 |

* cited by examiner

FIG. 9
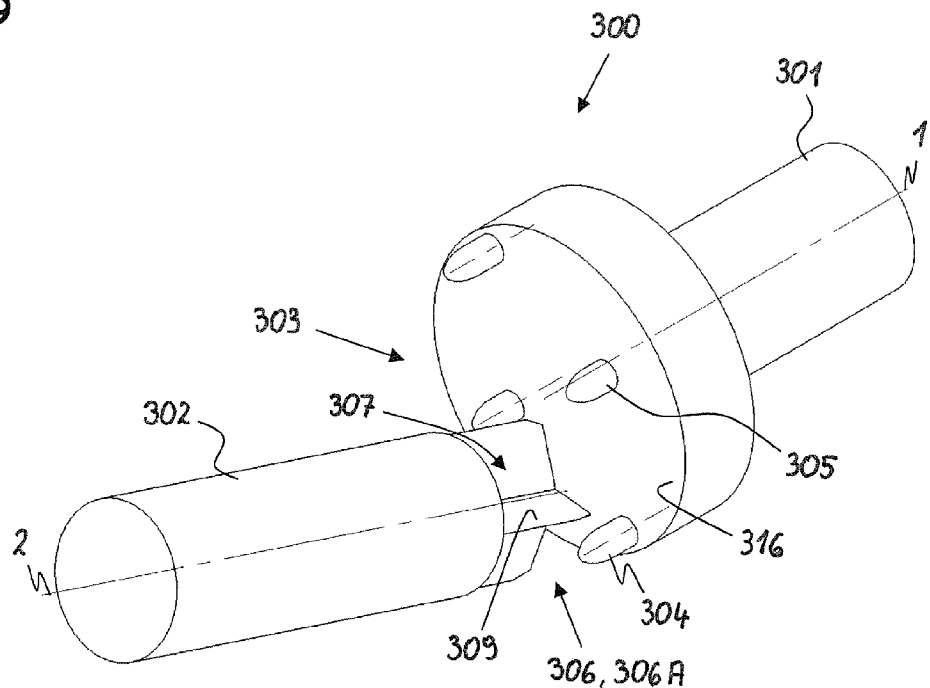
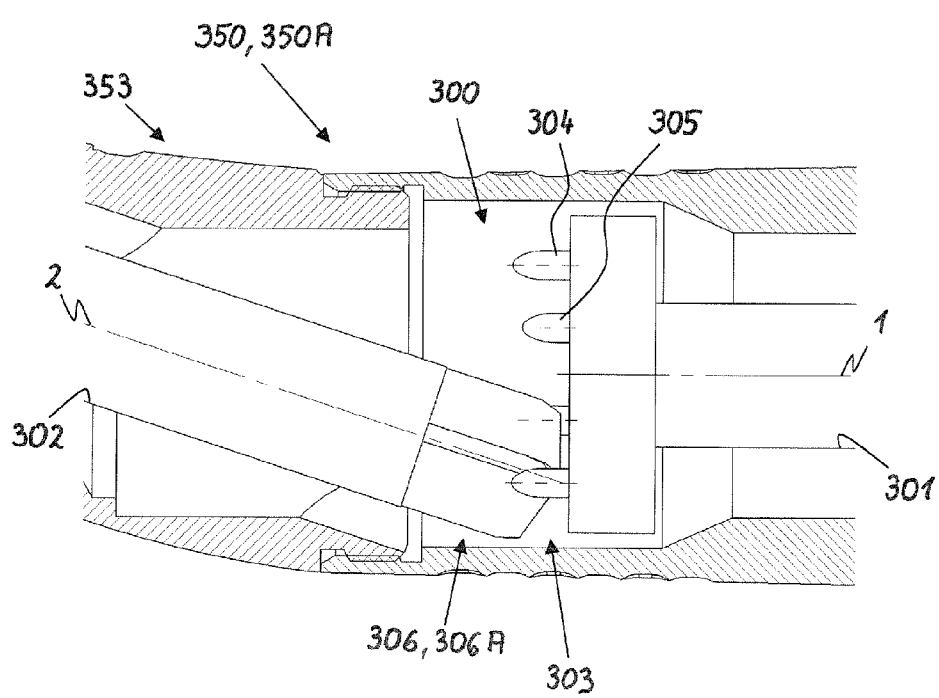
FIG. 10

FIG. 17
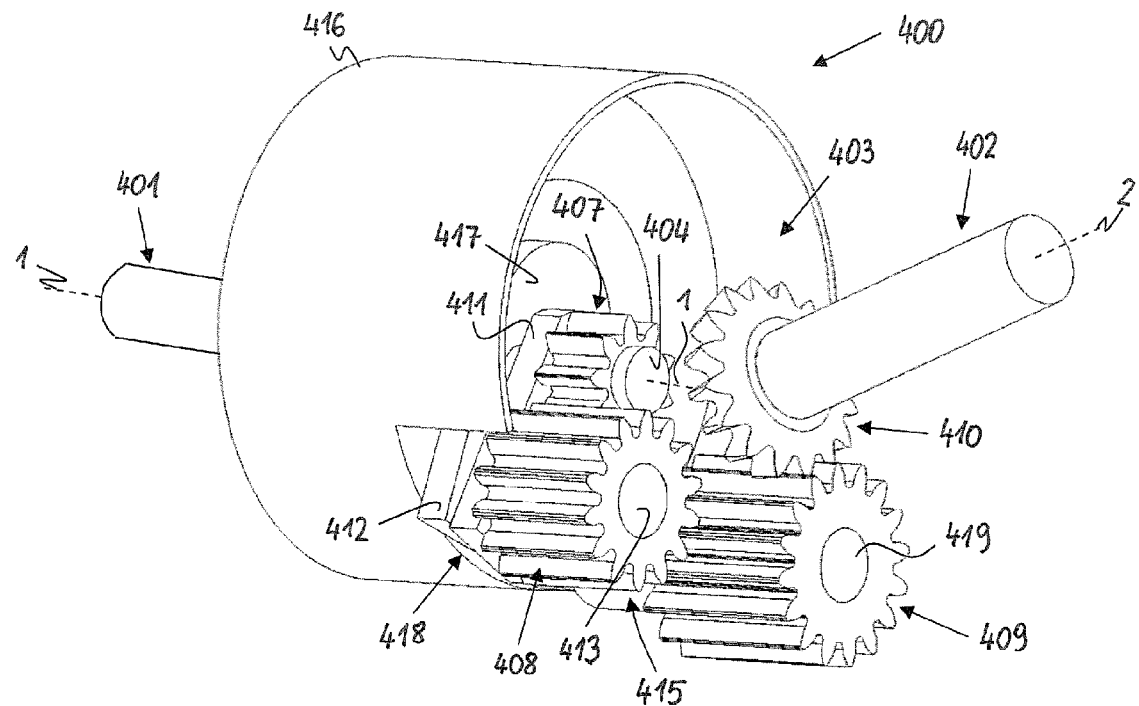
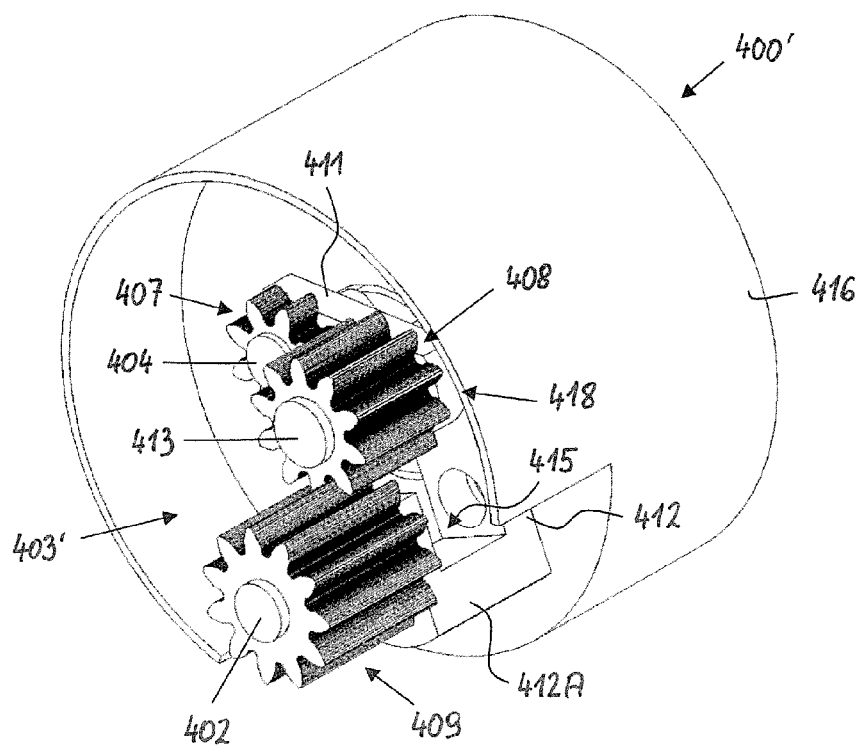
FIG. 18

DRIVE DEVICE FOR A MEDICAL, DENTAL OR SURGICAL TOOL

CROSS REFERENCE TO RELATED APPLICATION

This application is a U.S. bypass continuation application of International Application No. PCT/EP2014/060397, filed May 21, 2014, which in turn claims priority from European Patent Application No. EP 13168650.3, filed May 22, 2013, from abandoned European Patent Application No. EP 13168704.8, filed May 22, 2013, from abandoned European Patent Application No. EP 13171613.6, filed Jun. 12, 2013, and from abandoned European Patent Application No. EP 14165294.1, filed Apr. 18, 2014, which are incorporated herein by reference.

BACKGROUND

Field

The present application concerns a mechanical drive device for a medical, dental or surgical tool that is designed to put the tool into an oscillating, rotational motion. In that respect, an oscillating, rotational motion is understood to mean a rotational motion in which the tool alternately rotates by a first angle of rotation in a first rotational direction and by a second angle of rotation in a second rotational direction substantially opposing the first rotational direction, wherein the first and second angles of rotation have different values, so that, during multiple sequential rotations in the first and second rotational directions the tool cumulatively experiences a rotational motion in a preferred direction.

Description of Prior Art

Such a mechanical drive device is disclosed in patent application PCT/EP2012/073144. This drive device comprises a planetary gear train for the transmission of a rotational movement from a drive shaft to an output shaft and an eccentric gear unit which generates a reciprocating movement and also transmits it to the output shaft. By superimposing the rotational movement and the reciprocating movement, an oscillating rotational motion can be generated and/or the output shaft and a tool connected thereto may be put into such an oscillating rotational motion.

SUMMARY

It is an object of this application to create an alternative mechanical drive device that is designed to put a medical, dental or surgical tool into an oscillating, rotational motion, wherein the alternative drive device has one or more advantages over drive devices in the prior art, including, e.g., it has a simpler design, it is easier to manufacture, it has fewer elements, it is cost-effective to manufacture, and or it is smaller.

Described below is a (mechanical) drive device for a medical, dental or surgical tool that is designed to put the tool into an oscillating, rotational motion wherein the oscillating, rotational motion comprises an alternating rotation of the tool by a first angle of rotation in a first rotational direction and by a second angle of rotation in a second rotational direction substantially opposed to the first rotational direction, wherein the first and second angles of rotation have different values, so that, during multiple sequential rotations in the first and second rotational directions, the tool experiences a cumulative rotational motion in a preferred direction, wherein the drive device comprises: A drive shaft rotatable about a first rotational axis which is designed for the transmission of a drive movement, in particular in the form of a unidirectional rotational motion, an output shaft that can be put into an oscillating rotational motion and that can rotate about a second rotational axis, and an eccentric gear unit that connects the drive shaft and the output shaft, wherein the eccentric gear unit comprises at least one eccentric pin and at least one receiving unit or carrier unit for the eccentric pin, which work together or are designed in such a way that the output shaft and a tool that can be connected to the output shaft can be put into the oscillating rotational motion.

As will be explained in detail below, that means that only one gear unit, in particular only one eccentric gear unit, is provided for or needed in order to convert the drive movement provided by the drive shaft, in particular the unidirectional rotational motion, into the oscillating rotational motion. The eccentric gear unit is preferably designed in such a way that it can convert the drive movement/unidirectional rotational motion provided by the drive shaft into the oscillating rotational motion, and in particular transmit it to the output shaft, in particular alone or without another gear unit. This design of the eccentric gear unit is of considerable advantage in comparison with the transmission unit known from the prior art, in which, in addition to the eccentric gear unit generating only a reciprocating movement, a second gear unit is also required in order to generate the oscillating rotational motion, in particular in view of its simple, space-saving construction and cost-effective manufacture.

The eccentric gear unit is preferably supported by at least one bearing provided for on the drive shaft and/or on the output shaft, in particular a roller bearing or ball bearing. The eccentric gear unit is preferably made from metal and/or plastic. The eccentric gear unit is preferably penetrated by the first rotational axis of the drive shaft and/or the second rotational axis of the output shaft.

The receiving unit or carrier unit for the eccentric pin is preferably provided for on a substantially cylindrical surface surrounding the first rotational axis or the second rotational axis. The receiving unit or carrier unit preferably comprises at least one indentation, recess or groove. Particularly preferably, the receiving unit for the eccentric pin comprises a self-contained (endless) track or guide around the first rotational axis or the second rotational axis or the receiving unit itself forms such a self-contained (endless) track or guide around the first rotational axis or the second rotational axis. Particularly preferably, the receiving unit, in particular the track or guide, substantially extends in an undulating or curved manner around the first rotational axis or the second rotational axis, in particular on the substantially cylindrical surface surrounding the first rotational axis or the second rotational axis. The receiving unit or carrier unit preferably has at least one section or groove that extends substantially axially relative to the second rotational axis of the output shaft. The receiving unit, in particular the groove that extends substantially axially relative to the second rotational axis of the output shaft, preferably comprises a bottom surface that is tilted in at least one section in the direction of the second rotational axis of the output shaft, so that the receiving unit or the groove preferably has a varying depth in at least one section, in particular relative to a substantially cylindrical surface or outer surface in which the receiving unit or the groove is held.

According to one embodiment, the receiving unit or carrier unit or track for the eccentric pin comprises multiple sections arranged at angles to one another. The receiving unit preferably comprises multiple substantially Y-shaped sections that are connected with one another, in particular connected with one another on the lateral arms of the Y. The lateral arms of the Y are preferably offset somewhat from one another and/or relative to the vertical or third arm of the Y.

The receiving unit or carrier unit for the eccentric pin preferably comprises at least one first section that is formed in such a way that it causes a rotation of the output shaft in the first rotational direction, and a second section that is formed in such a way that it causes a rotation of the output shaft in the second rotational direction. Particularly preferably, the first section, which is formed in such a way that it causes a rotation of the output shaft in the first rotational direction, comprises multiple sub-sections arranged at a slant or an angle to one another. The first section and the second section are preferably of different lengths. In particular, the section that causes a rotational motion of the output shaft in the preferred direction is of a longer length than the section that causes a rotational motion of the output shaft in the direction opposite the preferred direction. The section that causes a rotational motion of the output shaft in the direction opposite the preferred direction is preferably located at one end of at least one lateral arm of a Y-shaped section of the receiving unit.

The receiving unit or carrier unit for the eccentric pin, in particular the groove, preferably comprises at least one section oriented essentially parallel to the second rotational direction of the output shaft, wherein this section in particular corresponds to the vertical arm of the Y-shaped section of the receiving unit described above. In particular, a first arm extends from this section oriented parallel to the second rotational axis of the output shaft in a first direction and a second arm in a second direction, wherein the second direction is different from the first direction. The angle between these two arms or the lateral arms of the Y is preferably greater than 90°.

Particularly preferably, the first arm comprises a first edge and the second arm a second edge, wherein the two edges meet at a contact point, wherein the contact point is arranged at a distance or horizontally offset from a central axis of the section oriented parallel to the second rotational axis of the output shaft, or is located outside the section oriented parallel to the second rotational axis of the output shaft. This arrangement of the contact point defines the rotation of the eccentric pin or the eccentric gear unit in a preferred direction, or the rotation of the eccentric pin or the eccentric gear unit in a particular direction, in particular in a direction opposite the preferred direction, is prevented or hindered. The two edges of the arms preferably delimit the arms, in particular the edges define the upper limit of the arms or grooves. The two arms in particular each have another edge, which defines the lower limit of the arms or grooves. The lower edges preferably merge into the section oriented essentially parallel to the second rotational axis of the output shaft or into the vertical arm of the Y-shaped section of the receiving unit.

According to this embodiment, the eccentric gear unit is designed in such a way that the eccentric pin moves in the groove or guide or track of the receiving unit or carrier unit, wherein, due to the configuration or form of the groove or guide or track described above the output shaft, which is in particular directly connected to or is integrally with the receiving unit, can be put into an oscillating rotational motion.

According to an alternative embodiment, the eccentric gear unit comprises a first eccentric pin, to which a first receiving unit or carrier unit is assigned, and a second eccentric pin, to which a second receiving unit or carrier unit is assigned. This eccentric gear unit is preferably designed in such a way that an eccentric pin and its assigned receiving unit move the output shaft in a first direction, for example in a preferred direction, and the other eccentric pin and its assigned receiving unit move the output shaft in a second direction, substantially opposite the first or preferred direction. The eccentric gear unit is preferably designed in such a way that the angles of rotation generated by the two receiving units have different values, so that the output shaft as a whole can be put into an oscillating rotational motion.

The first eccentric pin and the second eccentric pin are preferably spaced at different distances from the first rotational axis of the drive shaft. The drive shaft preferably comprises an end surface facing the output shaft, wherein an eccentric pin is located at or near the outer circumference of this end surface. The two eccentric pins are preferably provided for on a common line, wherein the line is oriented substantially at right angles to the first rotational axis of the drive shaft.

The first receiving unit and the second receiving unit are preferably at a distance from one another, in particular axially separate from one another relative to the second rotational axis of the output shaft. The first receiving unit and the second receiving unit are preferably separated from one another, for example by a recess.

The first receiving unit preferably comprises multiple first grooves and the second receiving unit multiple second grooves. The first and/or second grooves are preferably arranged essentially parallel to the second rotational axis of the output shaft. The first grooves and the second grooves are preferably offset from one another in such a way that there is alternately a first groove and a second groove.

The first receiving unit and the second receiving unit preferably surround the second rotational axis of the output shaft substantially in a circular shape. Particularly preferably, the first receiving unit and/or the second receiving unit are designed as disk-shaped or plate-shaped elements, through the centre of which the output shaft extends. Particularly preferably, the first receiving unit and/or the second receiving unit are designed as disk-shaped or plate-shaped elements, on the outer circumference or outer surface of which the first and second grooves are arranged. Particularly preferably, at least one receiving unit is formed or manufactured integrally with the output shaft.

The first grooves of the first receiving unit and the second grooves of the second receiving unit preferably surround the second rotational axis and/or the output shaft in a circular arrangement. The grooves of one receiving unit are preferably arranged evenly around the circumference of the receiving unit and/or around the second rotational axis of the output shaft and/or evenly spaced in relation to one another.

The eccentric gear unit is preferably designed in such a way that, alternately or not simultaneously, the first eccentric pin engages with the first receiving unit or carrier unit and the second eccentric pin with the second receiving unit or carrier unit. Alternatively and/or additionally, the eccentric gear unit is designed in such a way that, while one eccentric pin engages with its receiving unit or carrier unit in such a way that it causes a rotation of the output shaft, the other eccentric pin takes up a position in which it does not cause the output shaft to rotate.

According to another embodiment, the eccentric gear unit comprises multiple eccentric pins, wherein at least two of these multiple eccentric pins are at different distances from the first rotational axis of the drive shaft and/or the second rotational axis of the output shaft. The first rotational axis and/or the second rotational axis are preferably arranged centrally to the multiple eccentric pins. Particularly preferably, the eccentric gear unit comprises multiple eccentric pins, wherein at least two of these multiple eccentric pins can be moved on or are arranged on orbits that are spaced apart from one another. The first rotational axis or the second rotational axis preferably forms the central point for at least one of these orbits, in particular the central point for both orbits.

The carrier unit preferably comprises a tappet, with which the eccentric pins alternately engage and/or which they alternately contact. The tappet in particular comprises multiple sections separated from one another, with which the eccentric pins engage. The sections are, for example, formed by setbacks in the drive shaft or output shaft, by recesses in the drive shaft or output shaft, or by chambers. The setbacks, recesses, or chambers are in particular separated from one another by walls.

Preferably at least parts of the tappet, in particular at least parts of the sections of the tappet separated from one another, are arranged between the orbits on which at least two of the multiple eccentric pins move. Particularly preferably, a rotational axis of the tappet is located between the orbits on which at least two of the multiple eccentric pins move. Alternatively, the two orbits bisect the carrier unit or the tappet, in particular at areas or sections of the tappet that are located approximately opposite one another.

The eccentric pins are preferably arranged in such a way that eccentric pins which engage with the tappet and/or make contact with it consecutively engage with different sections of the tappet, in particular with different setbacks or chambers of the tappet, and/or make contact with different sections of the tappet, in particular different setbacks or chambers of the tappet.

The eccentric pins are preferably arranged in such a way that eccentric pins which engage with the tappet and/or make contact with it consecutively move the tappet in opposite rotational directions and/or through different angles of rotation.

The number of sections of the tappet and the number of eccentric pins is preferably between 2 and 12 in each case. The respective number of eccentric pins at different distances from the first rotational axis and/or the second rotational axis is preferably the same, for example two or four eccentric pins are located closer to the first rotational axis and two or four eccentric pins are located further away from the first rotational axis. The respective number of eccentric pins that can be moved on or that is located on orbits that are separate from one another is preferably the same, for example two or four eccentric pins are located on a first orbit and two or four eccentric pins are located on a second orbit. The number of separate sections of the tappet and the number of eccentric pins is preferably the same.

The carrier unit or the tappet is preferably provided for at one end of the output shaft. The output shaft preferably forms part of a multi-part shaft assembly for transmitting a drive movement to the tool. Particularly preferably, at one end of the output shaft opposite the end with the carrier unit or the tappet a gearwheel is provided for, for transmitting the oscillating rotational motion to the tool. This gearwheel is in particular designed in such a way that it transmits the oscillating rotational motion to a tool-holding device for the tool.

The first rotational axis of the drive shaft and the second rotational axis of the output shaft are preferably arranged at an angle to one another, wherein the angle is greater than 0°, and the angle is preferably between 5° and 45°. Alternatively, the first rotational axis of the drive shaft and the second rotational axis of the output shaft are located essentially parallel to one another and/or the angle between the two rotational axes is 0°.

A medical, in particular a dental or surgical, treatment device, preferably a medical, in particular a dental or surgical, hand grip element, which is in particular designed for endodontic treatments, is preferably equipped with a drive device that comprises an eccentric gear unit that is designed to convert the drive movement, in particular in the form of a unidirectional rotational motion, provided by the drive shaft into an oscillating rotational motion, particularly on its own or without another gear unit, and to in particular transmit it to the output shaft. Particularly preferably, the drive device is arranged in the treatment device or in the hand grip element in such a way that the first rotational axis of the drive shaft and the second rotational axis of the output shaft are arranged at an angle to one another, wherein the angle is greater than 0° and is in particular between 90° and 100°.

The treatment device or the hand grip element preferably comprises a head section with a tool-holding device for the tool, wherein, according to one embodiment, at least a part of the tool-holding device is located on the output shaft. Particularly preferably, a gripping section adjoins the head section, wherein the eccentric gear unit is at least partly located within the head section and/or in the gripping section and/or in an area that connects the head section to the gripping section. According to another embodiment, the eccentric gear unit is located in the gripping section, in particular in a bent or angular area of the gripping section.

According to another embodiment, a (mechanical) drive device is provided for a medical, in particular dental or surgical tool that is designed to put the tool into an oscillating rotational motion, wherein the oscillating rotational motion comprises an alternating rotation of the tool by a first angle of rotation in a first rotational direction and a second angle of rotation in a second rotational direction, essentially opposed to the first rotational direction, wherein the first and second angles of rotation preferably have different values, so that, during multiple sequential rotations in the first and second rotational directions the tool cumulatively experiences a rotational motion in a preferred direction, wherein the drive device comprises: A drive shaft assembly rotatable about a first rotational axis, which drive shaft assembly is designed to transmit a drive motion, in particular a unidirectional rotational motion, an output shaft that can be put into the oscillating rotational motion and can be rotated around a second rotational axis, and a transmission unit to transmit the drive motion from the drive shaft assembly to the output shaft in such a way that the output shaft and a tool that can be connected to the output shaft can be put into the oscillating rotational motion. The transmission unit comprises at least one drive-side transmission element and at least one output-side transmission element. Said at least one drive-side transmission element can be set in rotation around the first rotational axis by the drive shaft assembly. An operational connection between said at least one drive-side transmission element and said at least one output-side transmission element for transmitting the drive movement from the drive shaft assembly to the output shaft only exists during part of a complete revolution of said at least one drive-side transmission element around the first rotational axis of the drive shaft assembly. A complete revolution in this sense is understood to be a rotation by 360°.

The transmission unit preferably comprises a first output-side transmission element and a second output-side transmission element, wherein the transmission unit is designed in such a way that an operational connection can be established in an alternating or time-offset manner between said at least one drive-side transmission element and the first output-side transmission element and between said at least one drive-side transmission element and the second output-side transmission unit for the transmission of the drive motion from the drive shaft assembly to the output shaft.

Alternatively, the transmission unit may comprise a first drive-side transmission element and a second drive-side transmission element, wherein the transmission unit is designed in such a way that an operational connection can be established in an alternating or time-offset manner between said at least one output-side transmission element and the first drive-side transmission element and between said at least one output-side transmission element and the second drive-side transmission unit for the transmission of the drive motion from the drive shaft assembly to the output shaft.

Alternatively, the transmission unit may comprise a first drive-side transmission element and a first output-side transmission element, which in particular form a second gear unit, and a second drive-side transmission element and a second output-side transmission element, which in particular form a first gear unit, referred to repeatedly below as an eccentric gear unit, wherein the first drive-side and output-side transmission elements are designed to move the output shaft in the first rotational direction, and the second drive-side and output-side transmission elements are designed to move the output shaft in the second rotational direction. The drive-side transmission elements can be set in rotation around the first rotational axis by the drive shaft assembly. At least the first drive-side and output-side transmission element or the second drive-side and output-side transmission element or the first gear unit or the second gear unit are designed in such a way that an operational connection between the first drive-side and output-side transmission element or between the second drive-side and output-side transmission element for the transmission of the drive motion from the drive shaft assembly to the output shaft only exists during a part of a complete revolution of the drive-side transmission element around the first rotational axis of the drive shaft assembly.

Of course, it is also possible for the transmission unit to be designed in such a way that an operational connection between the first drive-side and output-side transmission element and the second drive-side and output-side transmission element for the transmission of the drive motion from the drive shaft assembly to the output shaft always only exists during a part of a complete revolution of a drive-side transmission element around the first rotational axis of the drive shaft assembly. The transmission unit is preferably designed in such a way that an operational connection can be established in an alternating or time-offset manner between the first drive-side and output-side transmission element (of the second gear unit) and between the second drive-side and output-side transmission elements (of the first gear unit or eccentric gear unit) to transmit the drive motion from the drive shaft assembly to the output shaft.

At least one drive-side transmission element or one output-side transmission element preferably comprises: a first section that can be operationally connected to the corresponding drive-side transmission element or output-side transmission element to transmit the drive motion from the drive shaft assembly to the output shaft, and a second section in which the operational connection between the drive-side transmission element and the output-side transmission element is released, so that there is no transmission of the drive motion from the drive shaft assembly to the output shaft. In regard to any preferred embodiments of the drive-side and output-side transmission elements and the first and second sections, we refer explicitly to the following embodiment of a drive device with an eccentric gear unit and a second gear unit.

The transmission unit preferably comprises multiple drive-side transmission elements, wherein the drive shaft assembly is designed to drive at least some of these multiple drive-side transmission elements simultaneously. The transmission unit preferably comprises multiple drive-side transmission elements, wherein the drive shaft assembly is designed to turn at least some of these multiple drive-side transmission elements in the same rotational direction. Both configurations have the advantage of simple construction and that in particular only one motorized drive is required.

The transmission unit is preferably designed in such a way that an operational connection between said at least one drive-side transmission element and a first output-side transmission element for the transmission of the drive movement from the drive shaft assembly to the output shaft also causes a movement of at least one additional drive-side transmission element, in particular a second gear unit. In particular the transmission unit is designed in such a way that this movement enables an operational connection between an additional drive-side transmission element, in particular a second gear unit, and the additional output-side transmission element.

The transmission unit preferably comprises multiple drive-side transmission elements, wherein the drive shaft assembly comprises a single drive shaft, on which at least some of these multiple drive-side transmission elements are located. This advantageously achieves a very simple construction for the drive device.

Alternatively, the transmission unit may comprise multiple drive-side transmission elements, wherein the drive shaft assembly comprises two preferably coaxially arranged drive shafts, wherein at least one of the multiple drive-side transmission elements is located on a first drive shaft and at least one of the multiple drive-side transmission elements is located on a second drive shaft. This advantageously allows different speeds to be transmitted via the drive shaft assembly. One of the two shafts is preferably designed as a hollow shaft, within which the other of the two shafts is located. Between the two drive shafts and/or on the two drive shafts there are preferably bearing elements and/or bearing points provided, in particular on the inside of the drive shaft designed as a hollow shaft.

The transmission unit preferably comprises multiple drive-side transmission elements, wherein at least two of these multiple drive-side transmission elements are spaced at different distances from the first rotational axis of the drive shaft assembly or can be moved by the drive shaft assembly on orbits with different radii. This, in particular in connection with a single or shared drive shaft, permits a particularly compact construction to be achieved. One drive-side element, in particular of a gear unit, is preferably surrounded by another drive-side element, in particular of another gear unit, or is arranged within the other drive-side element, in particular in its radial extension.

The transmission unit preferably comprises multiple output-side transmission elements, wherein at least some of these multiple output-side transmission elements are arranged concentrically around the second rotational axis. The multiple output-side transmission elements are preferably spaced apart from one another, in particular axially relative to the second rotational axis.

The drive shaft assembly and the output shaft are preferably arranged at an angle to one another in such a way that the first rotational axis of the drive shaft assembly extends between a first section of said at least one output-side transmission element and a second section of said at least one output-side transmission element or between at least a section of a first output-side transmission element of the transmission unit and at least a section of a second output-side transmission element of the transmission unit. Particularly preferably, the first rotational axis extends between those sections of said at least one output-side transmission element or elements which cause a movement in the different rotational directions or the transmission of the drive motion or the operational connection between the drive-side transmission element and the output-side transmission element.

The drive-side transmission element and the output-side transmission element of the first gear unit and/or the drive-side transmission element and the output-side transmission element of the second gear unit are preferably arranged and/or designed in such a way that an operational connection for the transmission of the drive motion from the drive shaft assembly to the output-side can be established only between the drive-side transmission element and the output-side transmission element of the first gear unit and the drive-side transmission element and the output-side transmission element of the second gear unit. Particularly preferably, the drive-side transmission elements can be moved by the drive shaft assembly on orbits with different radii and the output-side transmission elements are each located on the orbit of the corresponding drive-side transmission element of the first or second gear unit.

The transmission unit or the first gear unit and/or the second gear unit preferably comprise a positive gear unit, in particular a toothed gear unit or an eccentric gear unit, a force-fitting or frictional gear unit, or a magnetic gear unit. Configurations are in particular possible with different or the same types of gears for the transmission unit or the first and second gear units, for example the first gear unit and the second gear unit can each comprise a toothed gear unit, or the transmission unit can comprise a toothed gear unit and an eccentric gear unit, or the transmission unit can comprise an positive gear unit and a force-fitting gear unit, etc. Basically, each of the gear unit types listed above can be combined with the same or another gear unit type named to form a transmission unit with first and second gear units.

A medical, in particular a dental or surgical, treatment device, preferably a medical, in particular dental or surgical, hand grip element, which is designed in particular for endodontic treatments, is provided with a drive device, wherein the drive device comprises: a transmission unit for transmitting the drive motion from a drive shaft assembly to an output shaft in such a way that the output shaft and a tool that can be connected with the output shaft can be set into an oscillating rotational motion, wherein the transmission unit comprises at least one drive-side transmission element and at least one output-side transmission element. Said at least one drive-side transmission element can be set in rotation around the first rotational axis by the drive shaft assembly. An operational connection between said at least one drive-side transmission element and said at least one output-side transmission element for transmitting the drive movement from the drive shaft assembly to the output shaft only exists during a part of a complete revolution of said at least one drive-side transmission element around the first rotational axis of the drive shaft assembly.

The treatment device or the hand grip element comprises a head section with a tool-holding device for the tool, wherein at least a part of the tool-holding device is located on the output shaft. Alternatively, the treatment device or hand grip element can comprise a head section with a tool-holding device for the tool and a gripping section adjoining the head section, wherein the drive device is held in the gripping section.

The drive device described below is a preferred embodiment of the drive device described above with the transmission unit, in particular with the first gear unit and the second gear unit, in which an operational connection between the drive-side transmission element and the output-side transmission element for the transmission of the drive movement from the drive shaft assembly to the output shaft only exists during a part of a complete rotation of the drive-side transmission element around the first rotational axis of the drive shaft assembly. Accordingly, the features described in connection with this embodiment above are applicable in a corresponding manner to the following embodiment and may be combined with them, and vice versa.

According to this embodiment, a (mechanical) drive device is provided for a medical, in particular dental or surgical tool that is designed to set the tool into an oscillating rotational movement, wherein the oscillating rotational movement comprises an alternating rotation of the tool by a first angle of rotation in a first rotational direction and by a second angle of rotation in a second rotational direction, substantially opposed to the first rotational direction, wherein the first and second angles of rotation preferably have different values, so that, during multiple sequential rotations in the first and in the second rotational direction, the tool cumulatively experiences a rotational motion in a preferred direction, wherein the drive device comprises: A drive shaft rotatable about a first rotational axis, which is designed to transmit a drive movement, in particular a unidirectional rotational movement, an output shaft that can be set into the oscillating rotational motion and rotates around a second rotational axis, and a transmission unit which connects the drive shaft to the output shaft and which is designed to set the output shaft and a tool that can be connected to the output shaft into the oscillating rotational motion. The transmission unit comprises an eccentric gear unit with an eccentric pin and a receiving unit for the eccentric pin and a second gear unit. The drive shaft provides the eccentric pin or the receiving unit for the eccentric pin and a drive-side element of the second gear unit, wherein the drive-side element of the second gear unit is arranged concentrically with the first rotational axis of the drive shaft.

Advantageously, the drive device thus only comprises a drive shaft, in particular a single or shared drive shaft, to which both a (drive-side) transmission element of the eccentric gear unit and a drive-side element of the second gear unit are fastened. Thus the (drive-side) transmission element of the eccentric gear unit, as well as the drive-side element of the second gear unit can thus preferably be set into motion or rotation by the drive shaft.

The eccentric pin of the eccentric gear unit is preferably provided for on the drive shaft. Particularly preferably, the eccentric pin is provided for on a free end or on an end section of the drive shaft. Particularly preferably, the eccentric pin is formed integrally with the drive shaft. The eccentric pin can preferably be set by the drive shaft into a rotational motion along a first orbit. These preferred embodiments also apply correspondingly to the eccentric pins described in the embodiments above.

The receiving unit for the eccentric pin is preferably provided on the output shaft. Particularly preferably, the receiving unit is arranged concentrically around the second rotational axis of the output shaft.

The receiving unit of the eccentric gear unit preferably comprises multiple receiving elements separated or spaced from one another, into which the eccentric pin engages one after the next. Particularly preferably, each receiving element comprises a projection or extension that projects, in particular radially, from the output shaft or the second rotational axis. Particularly preferably, each receiving element, in particular each projection or extension, comprises at least a guide or a groove into which the eccentric pin can engage. Particularly preferably, each receiving element, in particular each guide or groove, is designed in such a way that engagement of the eccentric pin into at least a part of the guide or groove causes a rotation of the output shaft and any tool connected with it in the first or second rotational direction.

Particularly preferably, the receiving elements are separated from one another by notches or recesses between the projecting receiving elements. Particularly preferably, the notches or recesses are arranged in such a way that the eccentric pin can move through them in order to engage successively with the receiving element.

Said at least one groove or guide of each receiving element preferably comprises multiple groove sections arranged at an angle to one another and connected to one another. Particularly preferably, said at least one groove or guide comprises at least one section, in particular oriented substantially parallel to the second rotational axis of the output shaft, from which a first arm extends in a first direction and a second arm in a second direction, and in particular a third arm in a third direction, wherein the first, second, and third directions are different directions.

Each receiving element, in particular said at least one groove or guide of each receiving element, preferably comprises an entrance opening through which the eccentric pin enters the receiving element, and an exit opening through which the eccentric pin exits the receiving element. Particularly preferably, the entrance opening and the exit opening are spaced apart from one another, in particular being arranged on opposite sides of a receiving element. Particularly preferably, the entrance opening of a first receiving element is substantially opposite the exit opening of a second receiving element, in particular separated by a notch or a recess between two receiving elements.

The second gear unit preferably comprises an output-side element that is provided on the output shaft and arranged concentrically around the second rotational axis of the output shaft, wherein the drive-side element and the output-side element of the second gear unit can be operationally connected to transmit a drive motion from the drive shaft to the output shaft. Particularly preferably, the output-side element of the second gear unit is axially (relative to the second rotational axis) spaced from the output-side element of the eccentric gear unit, in particular from the receiving unit for the eccentric pin.

The drive-side element of the second gear unit and the drive-side element, in particular the eccentric pin, of the eccentric gear unit are preferably arranged or spaced apart from one another in such a way that the drive-side element of the second gear unit only connects to the output-side element of the second gear unit, and the drive-side element of the eccentric gear unit only connects to the output-side element of the eccentric gear unit to establish a motion transmitting connection. The output-side element of the second gear unit and the output-side element, in particular the receiving unit for the eccentric pin, of the eccentric gear unit are preferably arranged or spaced from one another in such a way that only the drive-side element of the second gear unit connects to the output-side element of the second gear unit in a connection transmitting movement, and the drive-side element of the eccentric gear unit connects to the output-side element of the eccentric gear unit in a connection transmitting movement.

The drive-side element and/or the output-side element of the second gear unit are preferably designed in such a way that the operational connection between the drive-side element and the output-side element for the transmission of a drive movement from the drive shaft to the output shaft only exists during a part of a complete rotation of the drive-side element around the first rotational axis. Particularly preferably, a corresponding relationship applies to the eccentric gear unit, that is, the drive-side element, in particular the eccentric pin, and/or the output-side element of the eccentric gear unit, in particular the receiving unit or the receiving elements for the eccentric pin, are designed in such a way that the operational connection between the drive-side element and the output-side element for the transmission of a drive movement from the drive shaft to the output shaft only exists during part of a complete revolution of the drive-side element around the first rotational axis.

The drive-side or the output-side element preferably comprises: a first section that can be operationally connected to the output-side element or the drive-side element for the transmission of a drive movement from the drive shaft to the output shaft, and a second section in which the operational connection between the drive-side element and the output-side element is released, so that there is no transmission of a drive movement from the drive shaft to the output shaft. Such a configuration of the drive-side or the output-side element is provided in the second gear unit, for example: Particularly preferably, in this case the output-side element comprises a gearwheel or a pinion and the first section of the drive-side element is toothed, in particular with teeth arranged on an arc, and the second section of the drive-side element is not toothed, in particular designed as a flat surface. The teeth of the first toothed section preferably project over the second non-toothed section in the direction of the output-side gearwheel. It is also possible for the drive-side element to have a gearwheel or a pinion and the output-side element to have the first and section sections.

The drive-side element of the second gear unit located on the drive shaft preferably surrounds the eccentric pin provided on the drive shaft or the receiving unit for the eccentric pin provided on the drive shaft. In particular, the drive-side element is further away from the first rotational axis of the drive shaft than the eccentric pin or the receiving unit. This advantageously permits a particularly compact construction.

The second gear unit preferably comprises a positive gear unit, in particular a toothed gear unit, a force-fitting or frictional gear unit, or a magnetic gear unit.

The second gear unit designed as a force-fitting gear unit preferably comprises a drive-side and an output-side element, wherein both elements have force-fitting or friction-fitting surfaces that contact one another or can be brought into contact with one another. In particular, the drive-side or the output-side element comprises: a first section that can be operationally connected to the output-side element or the drive-side element for the transmission of a drive movement from the drive shaft to the output shaft, and a second section in which the operational connection between the drive-side element and the output-side element is released, so that no there is no transmission of a drive movement from the drive shaft to the output shaft. Particularly preferably, the first section comprises at least one friction-fitting surface which projects over the second section, which is for example designed as a flat surface, so that only the friction-fitting surface of the first section can be brought into contact with the friction-fitting surface of the other element.

The second gear unit designed as a magnetic gear unit preferably comprises a drive-side and an output-side element, wherein both elements have magnetic areas or magnetic elements, in particular permanent magnets. In particular, the drive-side or the output-side element comprises: a first section that can be operationally connected to the output-side element or the drive-side element for the transmission of a drive movement from the drive shaft to the output shaft, and a second section in which the operational connection between the drive-side element and the output-side element is released, so that no there is no transmission of a drive movement from the drive shaft to the output shaft. Particularly preferably, the first section comprises at least one magnetic area or one magnetic element and in particular the second section comprises at least one non-magnetic area or (in comparison with the magnetic area of the first section) a magnetically weaker are or an area with no magnetic element. Particularly preferably the first section projects over the second section in the direction of the magnetic area or magnetic element of the second element.

The second gear unit is preferably designed to move the tool substantially in the first rotational direction, and the eccentric gear unit is designed to move the tool substantially in the second rotational direction.

The transmission unit is preferably designed in such a way that the second gear unit or the eccentric gear unit alternately transmits a drive movement from the drive shaft to the output shaft.

A medical, in particular dental or surgical, treatment device, preferably a medical, in particular dental or surgical, hand grip element which is in particular designed for endodontic treatments, is provided that comprises a drive device with a transmission unit, wherein the transmission unit connects the drive shaft to the output shaft of the treatment device and is designed to set the output shaft and a tool that can be connected to the output shaft into an oscillating rotational movement. The transmission unit comprises an eccentric gear unit with an eccentric pin and a receiving unit for the eccentric pin and a second gear unit. The drive shaft provides the eccentric pin or the receiving unit for the eccentric pin and a drive-side element of the second gear unit, wherein the drive-side element of the second gear unit is arranged concentrically with the first rotational axis of the drive shaft.

Particularly preferably, the treatment device, preferably the hand grip element, comprises a head section with a tool-holding device for the tool, wherein at least a part of the tool-holding device is located within the output shaft.

According to another embodiment, a medical, in particular dental or surgical, treatment device, preferably a medical, in particular dental or surgical, hand grip element which is in particular designed for endodontic treatments, is provided comprising a (mechanical) drive device for a medical, in particular dental or surgical, tool. The drive device is designed to set the tool into an oscillating rotational movement. The drive device comprises: A drive shaft rotatable about a first rotational axis that is designed to transmit a unidirectional rotational movement, an output shaft that can be set into an oscillating rotational motion and can be rotated around a second rotational axis, and a gear unit that connects the drive shaft and the output shaft, wherein the gear unit comprises a plurality of mutually engaged gearwheels, an eccentric pin which is operationally connected to the gearwheels and oriented eccentrically to the first rotational axis of the drive shaft and is connected to the drive shaft in such a way that it can be set into rotation by the drive shaft, a first carrier unit and a second carrier unit that are arranged at an angle to one another, wherein the first carrier unit and the second carrier unit can be moved relative to one another in such a way that the angle formed or confined by the two carrier units is variable.

This drive device is in comparison to the known drive device with the planetary gear and the eccentric gear unit, simpler, constructed of fewer elements, and requires less space. The first carrier unit and the second carrier unit are preferably movably connected relative to one another, for example by a shaft. The first carrier unit and the second carrier unit particularly preferably form a joint or a jointed connection. The two carrier units or the jointed connection are in particular designed or arranged in such a way that, during operation of the gear unit or the drive device, they move through a predetermined track or can be moved on a predetermined track.

Preferably, one carrier unit, in particular an end of a carrier unit, is directly provided on the eccentric pin and/or directly connected to the eccentric pin and/or movably or rotatably connected to the eccentric pin. Particularly preferably, therefore, the track described above, along which the two carrier units or the joined connect moves and/or the movement of the two carrier units relative to one another are defined by the movement or track of the eccentric pin.

The first carrier unit and the second carrier unit are preferably connected (mechanically) by a shaft, wherein particularly preferably at least one of the multiple gearwheels is located on this shaft. This advantageously increases the compactness of the gear unit. Particularly preferably, the gearwheel on this shaft engages at least two other gearwheels. Particularly preferably, the gearwheel on this shaft and at least one of the two carrier units are designed movably relative to one another and/or the gearwheel on this shaft is designed to rotate relative to at least one of the two carrier units. Preferably, the first carrier unit and the second carrier unit are connected to each other at one of their ends.

Preferably at least one of the two carrier units has an elongate and/or rod-like and/or plate-like form. Preferably at least one carrier unit comprises at least one bore or receptacle which for example holds the eccentric pin, the connection shaft for the two carrier units, or a shaft on which one of the multiple gearwheels is located.

The two carrier units are preferably axially offset (relative to the first rotational axis of the drive shaft or the second rotational axis of the output shaft) or are arranged behind one another. The two carrier units are preferably located in one or two planes oriented substantially parallel to one another, wherein these plane(s) are oriented substantially at right angles to the first rotational axis and/or to the second rotational axis. The two carrier units preferably move during operation of the device within one or two planes oriented substantially parallel to one another, wherein these plane(s)

are oriented substantially at right angles to the first rotational axis and/or to the second rotational axis.

At least one carrier unit is preferably connected directly to a gearwheel located on the output shaft.

The gear unit preferably comprises three or four gearwheels that engage with one another. The gear unit is also preferably designed to change the speed, particularly preferably to change the speed relative to the speed transmitted by the drive shaft, in particular for the reduction of speed. Preferably at least one of the multiple gearwheels is designed as a spur wheel; particularly preferably, several of the gearwheels have substantially parallel central or rotational axes and/or form a spur wheel gear unit. Each gearwheel preferably comprises its own separate shaft, onto which it is fastened and/or mounted rotatably. At least one of the multiple gearwheels can preferably slide relative to the first rotational axis or relative to the second rotational axis in such a way that the distance between said at least one gearwheel and the first rotational axis or the second rotational axis can be changed.

Preferably a first of the multiple gearwheels is connected in a non-rotating manner to the eccentric pin. Particularly preferably, this first gearwheel is arranged in such a way that it moves along the orbit of the eccentric pin. Particularly preferably, the first gearwheel is designed or arranged to rotate about the first rotational axis of the drive shaft, in particular without itself turning around its own central axis. Particularly preferably, the first gearwheel connected to the eccentric pin in a non-rotating manner can slide relative to one of the following elements in such a way that the distance between the first gearwheel and that element is variable: to the output shaft, to the second rotational axis of the output shaft, to a gearwheel located and/or fastened on the output shaft, to at least one carrier unit, to at least a gearwheel whose distance from the first rotational axis and second rotational axis is constant.

A second gearwheel is preferably provided that engages the first gearwheel connected to the eccentric pin in a non-rotating manner. The second gearwheel is preferably located on a shaft that is provided on at least one of the two or on both carrier elements, or which (mechanically) connects the two carrier elements.

The second gearwheel is preferably designed to rotate relative to the shaft on which it is located, and/or to the central axis of that shaft and/or to at least one of the two carrier elements. Particularly preferably, the second gearwheel can slide relative to the drive shaft and/or to the first rotational axis of the drive shaft in such a way that the distance between the second gearwheel and the drive shaft and/or the first rotational axis is variable. The distance between the second gearwheel and the first gearwheel and/or the distance between the second gearwheel and another gearwheel engaging the second gearwheel and/or the distance between the second gearwheel and a gearwheel whose distance from the first rotational axis and second rotational axis is constant and/or the distance between the central or rotational axis of the second gearwheel and the central or rotational axis of the other gearwheel mentioned is preferably constant.

The second gearwheel is preferably arranged in such a way that it can be moved back and forth along a track that is preferably substantially a circular arc. This track is preferably arranged between the drive shaft and the output shaft. This track is preferably arranged in a plane that is substantially at right angles to the drive shaft and/or to the output shaft.

At least a third gearwheel is preferably provided whose distance from the first rotational axis and the second rotational axis is constant. This gearwheel preferably engages the second gearwheel. The distance of this third gearwheel or its rotational axis from the second gearwheel or its rotational axis is preferably constant. The distance of the third gearwheel or its rotational axis from the first gearwheel or its rotational axis is preferably variable. The third gearwheel is preferably located on the output shaft and/or fastened onto it in a non-rotating manner. Alternatively, the third gearwheel can be connected to a fourth gearwheel that is fastened in a non-rotating manner to the output shaft, or it engages the fourth gearwheel. The third gearwheel is preferably provided on one of the two carrier elements; in particular the third gearwheel is designed to be able to rotate relative to the carrier element on which it is provided.

At least one gearwheel can preferably slide relative to another gearwheel in such a way that the distance between these two gearwheels is variable. Particularly preferably, the two gearwheels whose distance relative to each other is variable are the first gearwheel and the third gearwheel. Particularly preferably, the two gearwheels whose distance from one another is variable are arranged with an axial offset from one another (relative to the first rotational axis or the second rotational axis) in such a way that during operation of the drive device the two gearwheels can be moved axially into a position that overlaps at least partly, at least during a limited period of time. This permits advantageous angles of rotation to be generated in the oscillating rotational movement generated by the gear in one rotational direction (in particularly in the preferred or working direction), for example angles of rotation greater than 100°, preferably greater than 120°, in particular angles of rotation of about 150°.

The two gearwheels whose distance from one another is variable are preferably arranged in two planes oriented substantially parallel with one another, wherein these planes are oriented at an angle, in particular substantially at a right angle, to the first rotational axis and/or to the second rotational axis. These two planes are preferably axially offset from one another (relative to the first rotational axis or the second rotational axis). At least one of the gearwheels whose distance from one another is variable, for example the first gearwheel, preferably moves during operation of the gear unit in one of these planes relative to the other of the two gearwheels whose distance from one another is variable, for example the third gearwheel.

Preferably, one of the two gearwheels whose distance from one another is variable, in particular the third gearwheel, is connected in a rotating manner to one of the carrier elements, wherein the gearwheel and the carrier element are spaced apart from one another in such a way that during operation of the drive device, at least during a limited period of time, the other of the two gearwheels (the first gearwheel) and/or the other carrier element (provided on the eccentric pin) can be moved between the gearwheel and the carrier element that is connected to it in a rotating manner. Particularly preferably, there is a free space provided between one of the two gearwheels whose distance from one another is variable, in particular the third gearwheel, and one of the carrier elements, so that during operation of the drive device, at least during a limited period of time, the other of the two gearwheels whose distance from one another is variable, in particular the first gearwheel, and/or the other carrier element can move at least partly into the free space.

The first gearwheel and the second gearwheel are preferably provided on the first carrier element. Particularly preferably, the distance between the first gearwheel and the second gearwheel is constant. The third gearwheel is preferably provided on the second carrier element. Particularly preferably, the distance between the second gearwheel and the third gearwheel is constant.

The carrier elements or the jointed connection formed by the carrier elements and at least some of the multiple gearwheels preferably form a unit in which the gearwheels are moved or driven or shifted by the movement of the jointed connection, so that in particular as described above the gearwheels can slide along their tracks or in their planes and/or the distances of the gearwheels from one another are variable. The jointed connection or the unit preferably comprises a pivot point or a rotational axis that is located in particular in the second rotational axis of the output shaft or is identical to the second rotational axis. The carrier elements or the joined connection are in particular designed in such a way that their movement, particularly their movement caused by the eccentric pin, causes the rotation of the tool or the tool-holding device in the second rotational direction (in particular in the return direction) of the oscillating rotational movement.

The gear unit is preferably supported by at least one bearing provided on the drive shaft and/or on the output shaft, in particular a roller bearing or ball bearing. The gear unit is preferably made from metal and/or plastic.

According to one embodiment, the treatment device or the hand grip element comprises a head section with a tool-holding device for the tool and a gripping section adjoining the head section, wherein the drive device is provided in the gripping section, in particular in the area of a bend in the gripping section. The tool-holding device and the gear unit are preferably connected mechanically to one another, for example through the output shaft, so that the oscillating rotational movement generated by the gear unit can be transmitted to the tool-holding device.

These and other embodiments will be described below with reference to the following drawings.

BRIEF DESCRIPTION OF THE DRAWINGS

FIG. 9 shows a third embodiment of a drive device or an eccentric gear unit designed to set the tool into an oscillating rotational movement.

FIG. 10 shows the drive device or the eccentric gear unit of FIG. 9 in a medical, dental or surgical treatment device or in a medical, dental or surgical hand grip element.

FIG. 17 shows a first embodiment of a drive device with a drive shaft, an output shaft, and a gear unit that comprises multiple gearwheels interlocking with one another, an eccentric pin, a first carrier element and a second carrier element that are at an angle to one another.

FIG. 18 shows a second embodiment of a drive device with a drive shaft, an output shaft, and a gear unit that comprises multiple gearwheels interlocking with one another, an eccentric pin, a first carrier element and a second carrier element that are at an angle to one another.

DETAILED DESCRIPTION

Figure 1:
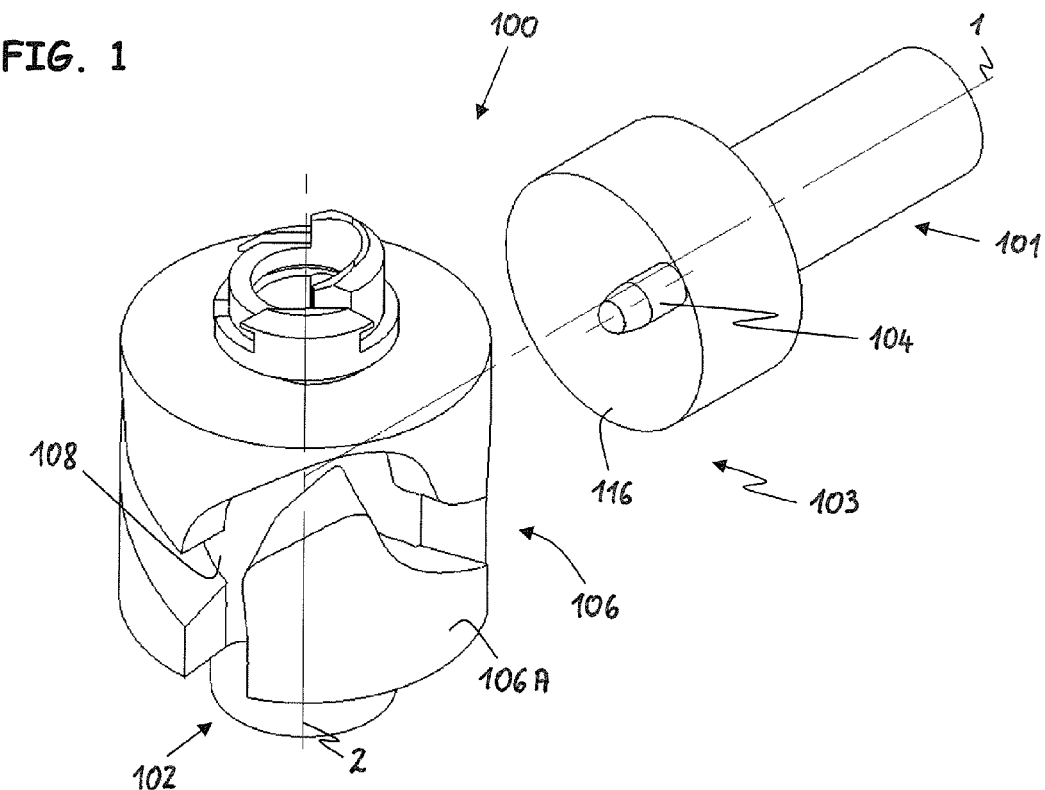
FIG. 1 shows a first embodiment of a drive device or an eccentric gear unit that is designed to set the tool into an oscillating rotational motion, wherein, in the interest of clarity, the two main elements are separated from one another.

The drive devices 100, 200, 300, 500, 600, 700, 800 shown in FIGS. 1-7 and 9-16 for a medical, dental or surgical tool are designed to set a tool into an oscillating rotational movement, wherein the oscillating rotational movement comprises an alternating rotation of the tool by a first angle in a first rotational direction and by a second angle in a second rotational direction substantially opposed to the first rotational direction, wherein the first and the second angles particularly have different values, so that, during multiple sequential rotations in the first and in the second rotational direction the tool experiences in total a rotational movement in a preferred direction. The tools that can be connected to drive devices 100, 200, 300, 500, 600, 700, 800 are preferably endodontic tools, for example files, in particular tools for the processing of the root canal.

The drive devices 100; 200; 300; 500; 600; 700; 800 comprise a drive shaft assembly 501; 601; 701 and/or drive shaft 101; 201; 301; 501A; 601A; 701A; 801 rotating about a first rotational axis 1 and designed to transmit a drive movement, in particular in the form of a unidirectional rotational movement, an output shaft 102; 202; 302; 502; 602; 702; 802 that can be set into the oscillating rotational movement and that can rotate about a second rotational axis 2, and an eccentric gear unit 103; 203; 303; 503; 603; 703; 803 that (mechanically) connects the drive shaft or drive shaft assembly 501; 601; 701; 101; 201; 301; 501A; 601A; 701A; 801 to the output shaft 102; 202; 302; 502; 602; 702; 802. The drive shaft or drive shaft assembly 501; 601; 701; 101; 201; 301; 501A; 601A; 701A; 801 is connected to or can be connected to a drive unit, for example to a motor, in particular an electric motor. The drive shaft or drive shaft assembly 501; 601; 701; 101; 201; 301; 501A; 601A; 701A; 801 is preferably supported by a bearing 115, in particular in a treatment device 150; 250; 350; 550 or in a hand grip element 150A; 250A; 350A; 550A.

The eccentric gear unit 103; 203; 303; 503; 603; 703; 803 comprises at least one eccentric pin 104; 204, 205; 304, 305; 505; 605; 705; 805 and at least one receiving unit or carrier unit 106; 206, 207; 306; 507; 607; 707; 806 for the eccentric pin 104; 204, 205; 304, 305; 505; 605; 705; 805 that work together in such a way that the output shaft 102; 202; 302; 502; 602; 702; 802 and a tool that can be connected to the output shaft 102; 202; 302; 502; 602; 702; 802 can be set in an oscillating rotational movement. According to different embodiments, the eccentric gear unit is either design so that exclusively the eccentric gear unit 103; 203; 303; 803 or the eccentric gear unit 503, 603, 703 together with a second gear unit 531, 631, 731 set the output shaft 102; 202; 302; 502; 602; 702; 802 and a tool that can be connected to it into the oscillating rotational movement.

Said at least one eccentric pin 104; 204, 205; 304, 305; 505; 605; 705; 805 is provided on an end surface 116; 216; 316; 516; 816 of the drive shaft or drive shaft assembly 501; 601; 701; 101; 201; 301; 501A; 601A; 701A; 801, wherein the end surface 116; 216; 316; 516; 816 is in particular facing the output shaft 102; 202; 302; 502; 602; 702; 802. Said at least one eccentric pin 104; 204, 205; 304, 305; 505, 605; 705; 805 or at least one of multiple eccentric pins 204, 205; 304, 305 are preferably located at or near the outer edge of the end surface 116; 216; 316; 516; 816. The end surface 116; 216; 316; 516; 816 preferably has a greater outer diameter than the drive shaft or drive shaft assembly 501; 601; 701; 101; 201; 301; 501A; 601A; 701A; 801.

The receiving unit or carrier unit 106; 206, 207; 306; 507; 607; 707; 806 for the eccentric pin 104; 204, 205; 304, 305; 505, 605; 705; 805 is preferably provided on the output shaft 102; 202; 302; 502; 602; 702; 802 and is in particular formed integrally with the output shaft 102; 202; 302; 502; 602; 702; 802. The receiving unit or carrier unit 106; 206, 207; 306; 507; 607; 707; 806 and/or at least a track 108; 808 or groove 209, 210; 508 provided on it surround the output shaft 102; 202; 302; 502; 602; 702; 802 in a circular or circular arc formation or are arranged substantially concentrically to the second rotational direction 2.

The output shaft 102; 202; 302; 502; 602; 702; 802 is preferably designed as a hollow shaft in which at least part of the tool and/or at least part of a tool-holding device 152, 252, 552 can be held or is held. The output shaft 102; 202; 302; 502; 602; 702; 802 and the elements connected to it in a non-rotating manner, for example the receiving unit or carrier unit 106; 206, 207; 507; 607; 707; 806 or the tool-holding device 152; 252; 552, are supported movably or rotatably by at least one bearing in a head section 151; 251; 551 of the treatment device 150; 250; 550 or of the hand grip element 150A; 250A; 550A.

Figure 8:
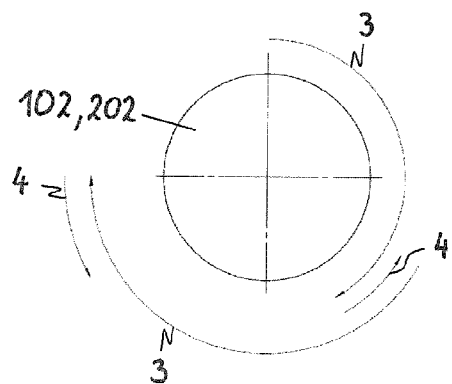
FIG. 8 shows a schematic example of an oscillating rotational movement as it can be generated by a drive device that converts a drive movement, in particular a unidirectional rotational movement, into an oscillating rotational movement.

The oscillating rotational movement generated by the drive device 100; 200; 300; 500; 600; 700; 800 or transmission unit 530; 630; 730 or eccentric gear unit 103; 203; 303; 803 and transmitted to the output shaft 102; 202; 302; 502; 602; 702; 802 and/or a tool connected to it is shown in FIG. 8: The output shaft 102; 202; 302; 502; 602; 702; 802 or the tool rotate alternately in a first rotational direction 3 (for example in a preferred or working direction in which the tool removes material, preferably tissue, in particular tissue of a dental root canal) by a first angle of rotation and in a second rotational direction 4 (opposite the preferred or working direction, for example called the return direction, in which in particular the removed material is carried away by the tool), which is substantially opposite the first rotational direction 3, by a second angle of rotation, wherein the first and the second angles of rotation have different values. According to the embodiment shown, for example, the angle of rotation in the first rotational direction 3 is about 150° and the angle of rotation in the second rotational direction 4 is about 30°. Clearly, other arbitrary values are possible for the angle of rotation, as long as the values of the angles of rotation differ, for example by about 45° and 20°, 180° and 90°, 270° and 90°, etc. The rotational directions shown in FIG. 8 are also an example only, so it is just as possible to reverse the rotational directions of the two rotational movements 3, 4 shown in FIG. 8, that is, rotational direction 3 would then be counterclockwise and rotational direction 4 clockwise. Of course, it is also possible for both angles of rotation to have the same measure, for example about 90°, 180°, or 360°.

The frequency of the oscillation movement of the drive shaft 102; 202; 302; 502; 602; 702; 802 or of the tool, for example, lies in a range of about 3-50 Hertz, preferably in the range from about 5-20 Hertz, in particular about 10 Hertz.

FIGS. 4, 7, 10, and 12 show the drive device 100; 200; 300; 500 or eccentric gear unit 103; 203; 303; 503 or the transmission unit 530 in a medical, in particular dental or surgical, treatment device 150, 250, 350, 550 and/or in a medical, in particular dental or surgical, hand grip element 150A, 250A, 350A, 550A. The treatment device 150; 250; 350; 550 or hand grip element 150A; 250A; 350A; 550A preferably comprise a contra-angel handpiece with a head section 151; 251; 551 and an adjoining gripping section 153; 253; 353; 553. In the head section 151; 251; 551, for example, there are the output shaft 102; 202; 502, in which at least part of a tool-holding device 152; 252; 552 is located, and at least a part of the eccentric gear unit 103; 203; 303; 503, in particular the receiving unit or carrier unit 106; 206; 306; 507, or a part of the transmission unit 530. A tool receptacle opening 154; 254; 554 is provided on the side of the head section 151; 251; 551. The output shaft 102; 202; 502 and/or the receiving unit or carrier unit 106; 206; 507 are held in the head section 151; 251; 551 in such a way that the second rotational axis 2 is oriented at an angle to the first rotational axis 1. As particularly discernible in FIG. 10, the drive device 100; 200; 300; 500 or eccentric gear unit 103, 203; 303; 503 can however also be completely within the gripping section 353; 553 and/or at a distance from the head section 151; 251; 551 or the tool-holding device 152; 252; 552.

Figure 4:
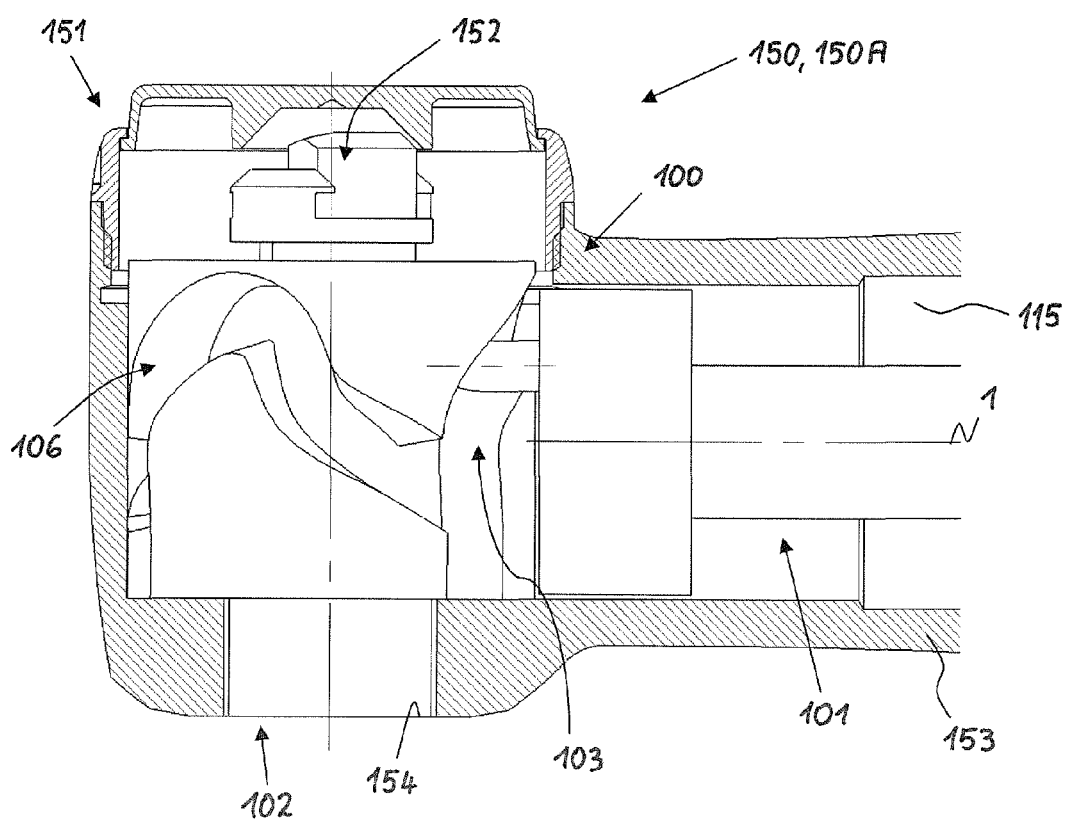
FIG. 4 shows a medical, dental or surgical treatment device or a medical, dental or surgical hand grip element with a drive device or an eccentric gear unit as shown in FIG. 1.
Figure 5:
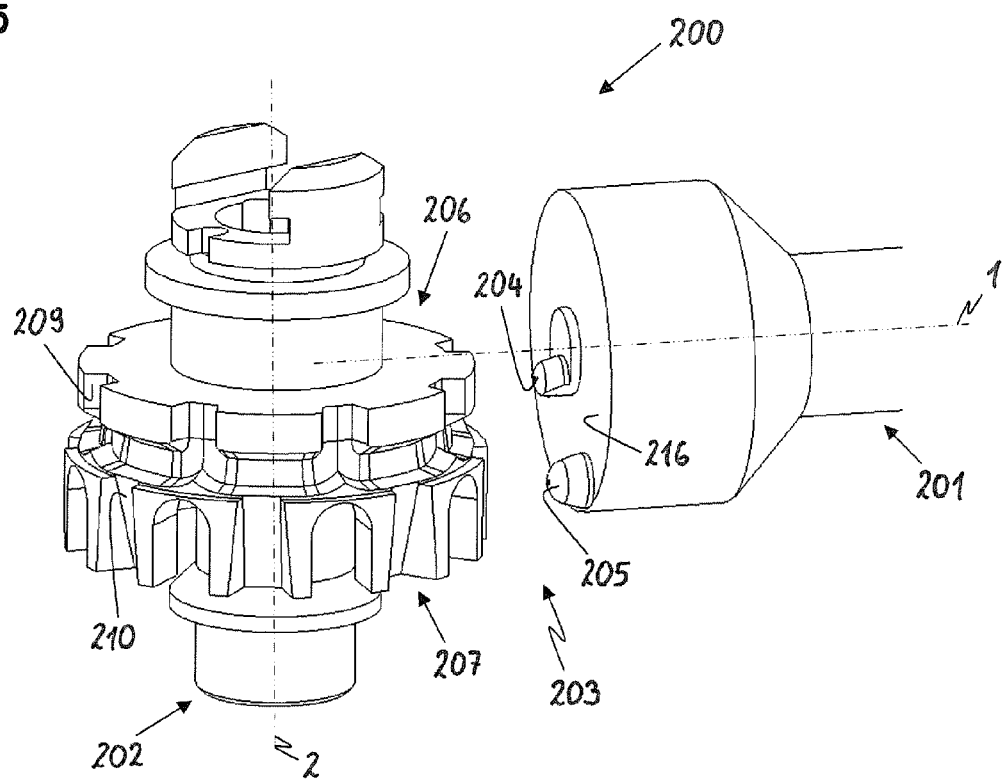
FIG. 5 shows a second embodiment of a drive device or an eccentric gear unit that is designed to set the tool into an oscillating rotational motion, wherein, in the interest of clarity, the two main elements are separated from one another.
Figure 6:
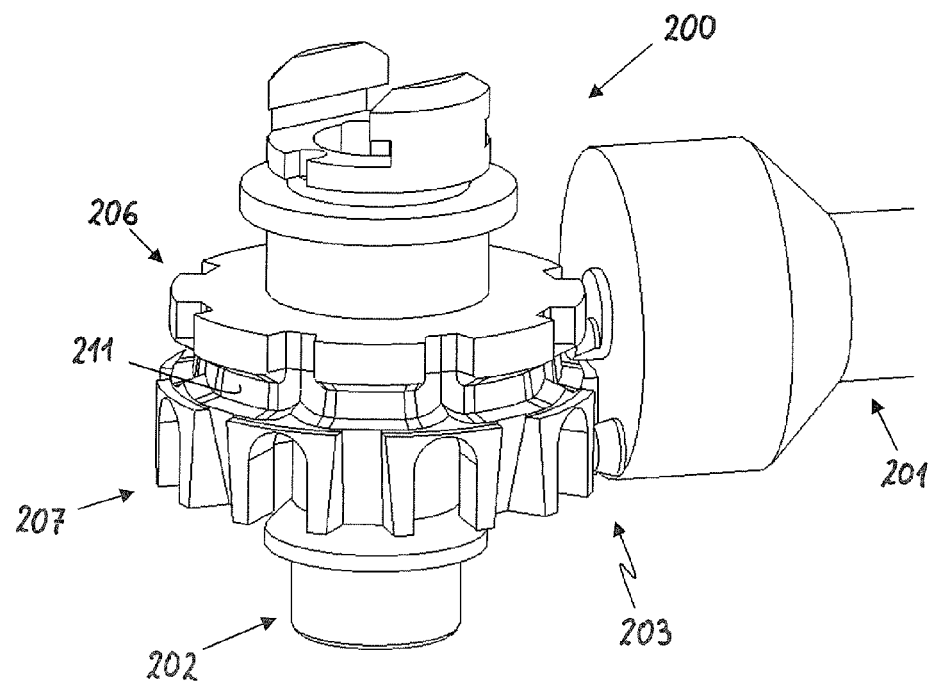
FIG. 6 shows the drive device or the eccentric gear unit of FIG. 5 in its assembled, operational ready state.
Figure 7:
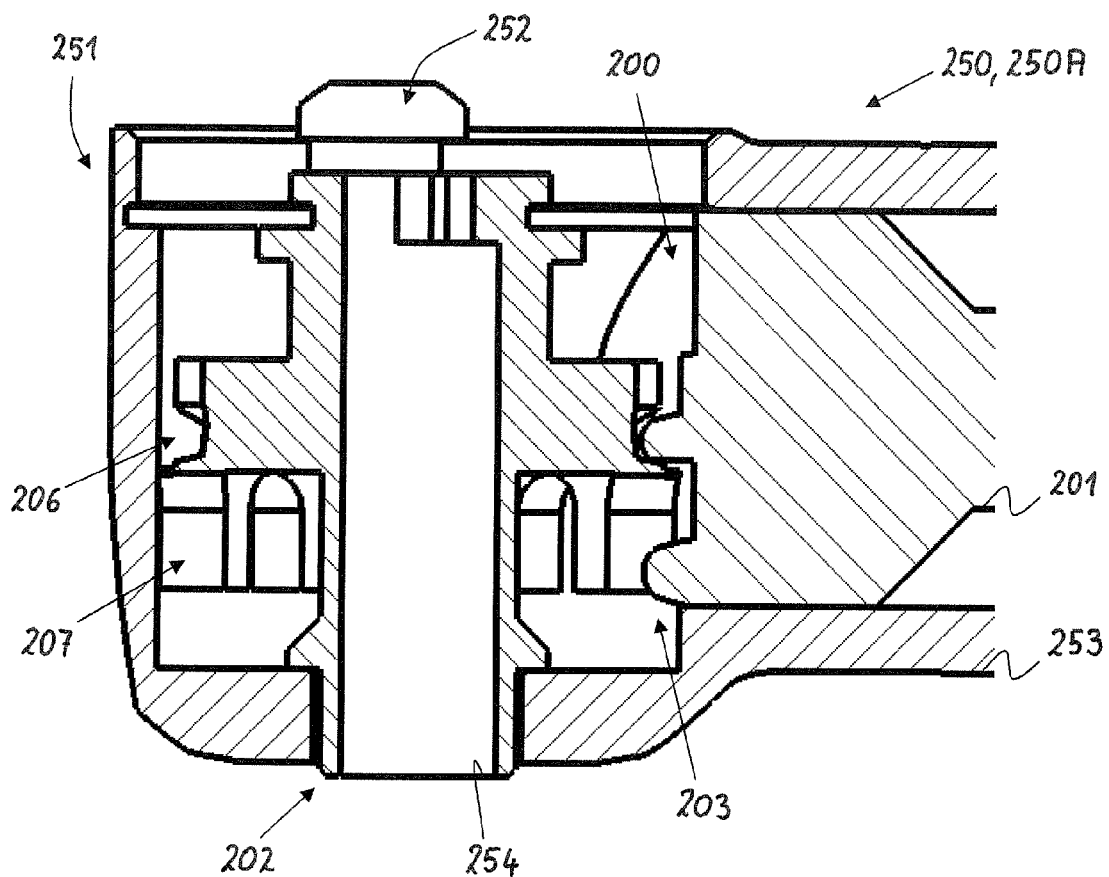
FIG. 7 shows a medical, dental or surgical treatment device or a medical, dental or surgical hand grip element with a drive device or an eccentric gear unit as shown in FIG. 5.
Figure 12:
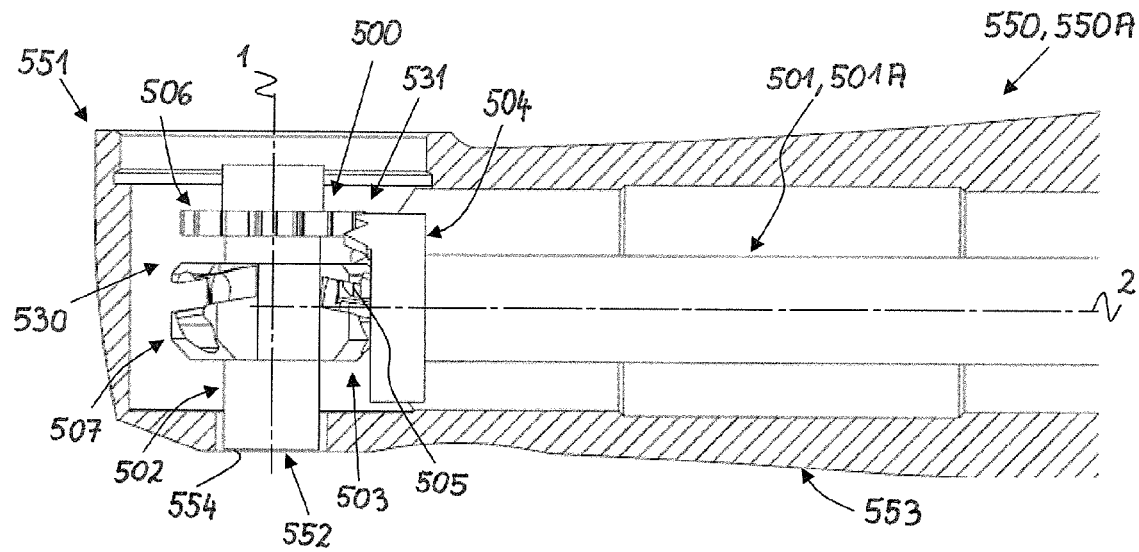
FIG. 12 shows a fourth embodiment of a drive device with a transmission unit that is designed to set the tool into an oscillating rotational movement.
Figure 14:
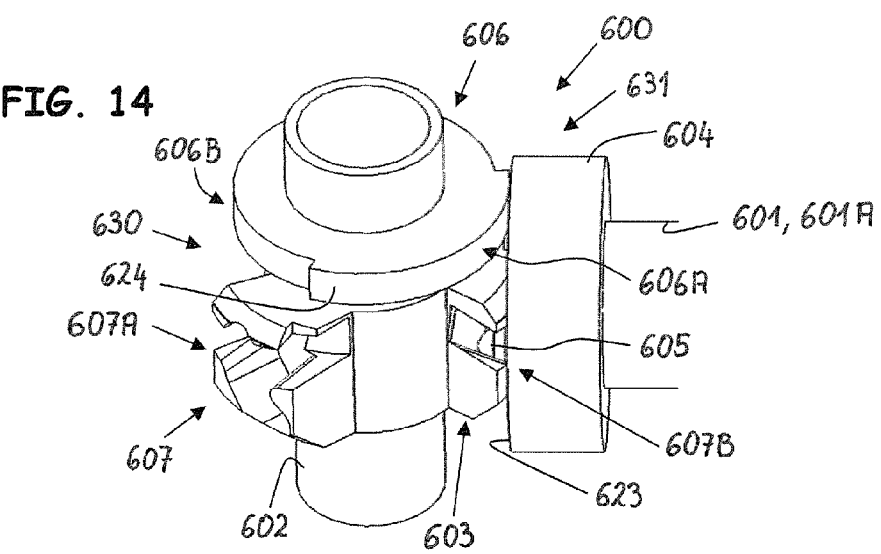
FIG. 14 shows a fifth embodiment of a drive device with a transmission unit that is designed to set the tool into an oscillating rotational movement.
Figure 15:
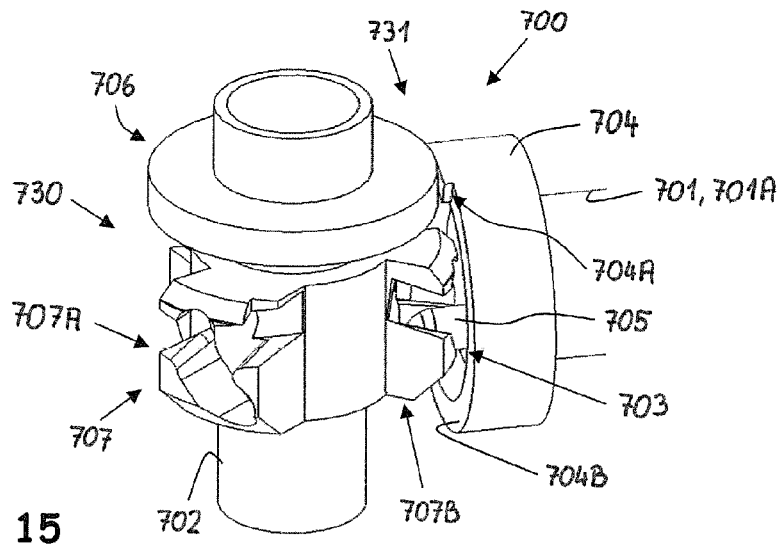
FIG. 15 shows a sixth embodiment of a drive device with a transmission unit that is designed to set the tool into an oscillating rotational movement.

The drive devices 600, 700 or transmission units 630; 730 or eccentric gear units 603; 703 shown in FIGS. 14 and 15 can be implemented in a corresponding manner in the treatment device 150; 250; 350; 550 and/or in the hand grip element 150A; 250A; 350A; 550A, in particular as shown in FIG. 12 for the drive device 500 or the transmission unit 530. The drive device 800 or eccentric gear unit 803 shown in FIG. 16 can be implemented in a corresponding manner in the treatment device 150, 250, 350, 550 and/or in the hand grip element 150A, 250A, 350A, 550A, in particular as shown in FIG. 4 for the drive device 100.

Figure 2:
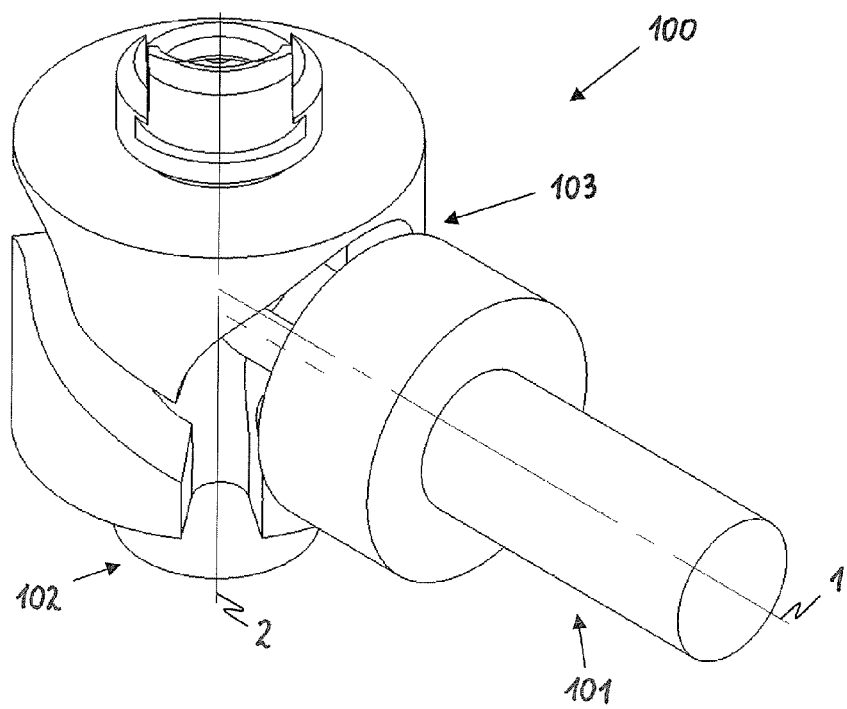
FIG. 2 shows the drive device or the eccentric gear unit of FIG. 1 in its assembled, operational ready state.

Further characteristics of drive device 100 will be described in the following (see FIGS. 1-4): As can be seen in FIGS. 1, 2, drive device 100 or eccentric gear unit 103 comprises a single eccentric pin 104.

The receiving unit or carrier unit 106 is in particular formed by a cylindrical body 106A, in which a self-contained track or guide 108 is provided for the eccentric pin 104. The self-contained track or guide 108 is in particular provided on the outer surface or sheath surface of cylindrical body 106A. The cylindrical body 106A is penetrated centrally or along its longitudinal axis 2 by output shaft 102.

The track or guide 108 is in particular self-contained in such a way that it forms a sinuous or axially (relative to the second rotational axis 2) upwards and downwards trending circle, in the center of which the second rotational axis 2 and/or the output shaft 102 is/are arranged.

Figure 3:
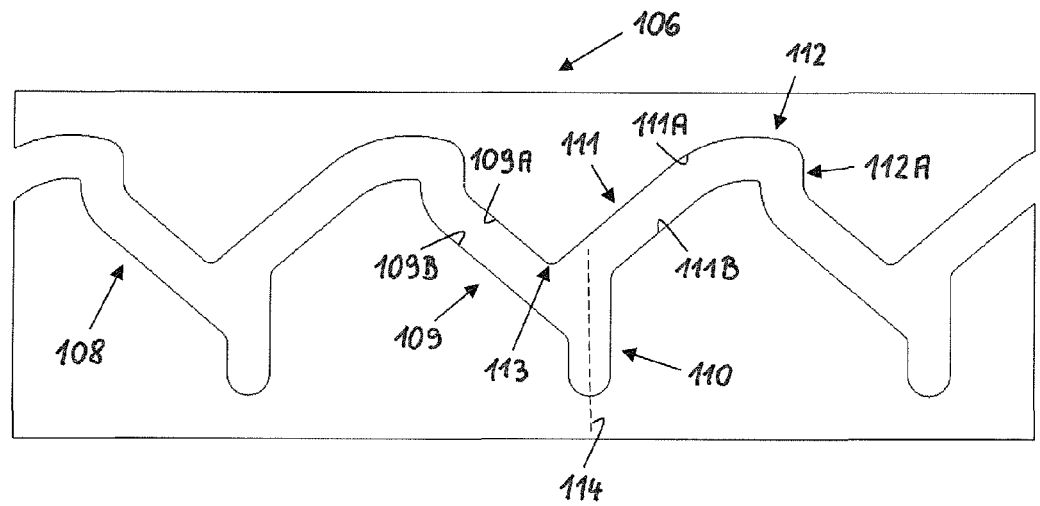
FIG. 3 shows an embodiment of a receiving unit or track for the eccentric pin of the drive device or the eccentric gear unit of FIG. 1 as a two-dimensional representation.

An example path for a groove or track 108 is shown in FIG. 3, wherein in the interest of better understanding the path of the groove or track 108 or the outer surface of cylindrical body 106A are shown in two dimensions: The receiving unit 106 or track 108 have multiple section 109-112 arranged at angles to one another. Sections 109-112 preferably form a substantially Y-shaped pattern, so that three Y-shaped patterns can be seen in FIG. 3, connected to one another at the ends of their arms.

The receiving unit 106 or track 108 for eccentric pin 104 preferably comprises at least a first section 109, 110, 111 that is shaped in such a way that it causes a rotation of the output shaft 102 in a first rotational direction, in particular in the preferred or working direction. Furthermore, receiving unit 106 or track 108 also comprises at least a second section 112, which is shaped in such a way that it causes a rotation of the output shaft 102 in the second rotational direction, in particular in a direction substantially opposite the preferred direction, or in a return direction.

The second section 112 preferably adjoins at least one of the first sections 109-111, in particular at least one end of the first section 109-111 or the second section 112 connects two first sections 109-111. The second section 112 is preferably provided in a peak area or vertically/axially (relative to second rotational axis 2) outer area of track 108. The second section 112 preferably has at least a subsection 112A which is oriented substantially parallel to the second rotational axis 2 of the output shaft 102.

The receiving unit or carrier unit 106 or the track 108 for eccentric pin 104 performance comprises at least one section 110 oriented substantially parallel with the second rotational axis 2 of the output shaft 102, from which in particular the first section or arm 109 extends in a first direction and a second section or arm 111 in a second direction that is different from the first direction. The section 110 can be closed at its free end or at its end facing away from sections 109-111 (see FIG. 3) or it can be open and/or have an opening (see FIGS. 1, 2). The section 110 is preferably located in a peak area or lower area of track 108, so that in particular sections 110 and 112 are located on opposing vertical or axial (relative to the second rotational axis 2) end areas of track 108.

The first arm 109 preferably comprises a first edge 109A and the second arm 111 a second edge 111A, wherein the two edges 109A, 111A join at a contact point 113 and wherein the contact point 113 is spaced from a central axis 114 of the section 110 oriented parallel with the second rotational axis 2 of output shaft 102. In particular, contact point 113 is arranged laterally to central axis 114 or, as seen from central axis 114, offset in the direction of a section 109, 111. This arrangement of the contact point 113 particularly defines a preferred direction of movement for the eccentric pin 104 or eccentric gear unit 103.

The two edges 109A, 111A as well as another edge or lower edge 109B, 111B delimit the sections or arms 109, 111, wherein the edges 109A, 111A in particular form the upper edges or are those edges, which are further away from section 110 than edges 109B, 111B.

The angles between sections 109, 110, 111 are preferably each greater than 90°: The angle between section 110 and section 109 or 111 is in particular greater than 125°, the angle between section 109 and section 111 is in particular about 95°-110°.

Further characteristics of drive device 200 will be described in the following (see FIGS. 5-7): The drive device 200 or eccentric gear unit 203 have multiple, for example two, eccentric pins 204, 205. The first eccentric pin 204 is preferably assigned a first receiving unit or carrier unit 206, and the second eccentric pin 205 a second receiving unit or carrier unit 207, wherein correspondingly the first eccentric pin 204 is designed to engage with the first receiving unit 206 or to work together with it, and the second eccentric pin 205 is designed to engage with the second receiving unit 207 or to work together with it.

The first eccentric pin 204 and the second eccentric pin 205 are at different distances from the first rotational axis 1 of the drive shaft 201. The eccentric pins 204, 205 preferably lie on a common line that extends at right angles from the first rotational axis 1 or intersects it.

The receiving units or carrier units 206, 207 each comprise a circular plate or disk on whose outer surface or circumference multiple grooves 209, 210 are provided. The receiving units 206, 207 enclose the output shaft 202, in particular in a circular shape, and/or they are arranged concentrically to the second rotational axis 2. The first receiving unit 206 and the second receiving unit 207 are preferably separated from one another by recess 211.

The first grooves 209 and the second grooves 210 are preferably offset from one another in such a way that there is alternately arranged a first groove 209 and a second groove 210. The grooves 209, 210 preferably extend along the second rotational axis 2 and/or substantially parallel with the second rotational axis 2. Preferably at least the bottoms of some grooves 209, 210 are tilted in the direction of the second rotational axis 2. The first grooves 209 and the second grooves 210 preferably surround the second rotational axis 2 in a circular arrangement.

The eccentric gear unit 203 is designed in such a way that during operation alternately the first eccentric pin 204 engages the first receiving unit 206 and the second eccentric pin 205 the second receiving unit 207. Alternatively or additionally, the eccentric gear unit 203 is designed in such a way that during operation, while one eccentric pin 204, 205 engages its receiving unit 206, 207 in such a manner that it causes a rotation of the output shaft 202, the other eccentric pin 204, 205 takes up a position in which it causes no rotation of the output shaft 202.

Further characteristics of drive device 300 will be described in the following (see FIGS. 9-11): The drive device 300 or eccentric gear unit 303 comprise a plurality of eccentric pins 304, 305, for example four, six, or eight. It can particularly be seen in FIG. 9 that at least two of these several eccentric pins 304, 305 are (radially) at different distance from the first rotational axis 1 of drive shaft 301 and/or from the second rotational axis 2 of output shaft 302. In particular, two eccentric pins 304 are provided substantially on the outer edge or outer circumference of the end surface 316, in contrast with which two other eccentric pins 305 are arranged offset towards the center of the end surface or towards the first rotational axis 1. Particularly preferably, the eccentric pins 304, 305, which are at different distances from rotational axes 1, 2, are arranged at an offset from or angle to one another, in particular in such a way that a first line from the eccentric pin 304 to the rotational axis 1 or 2 and a second line from the eccentric pin 305 to the rotational axis 1 or 2 subtends an angle greater than 0°.

Figure 11:
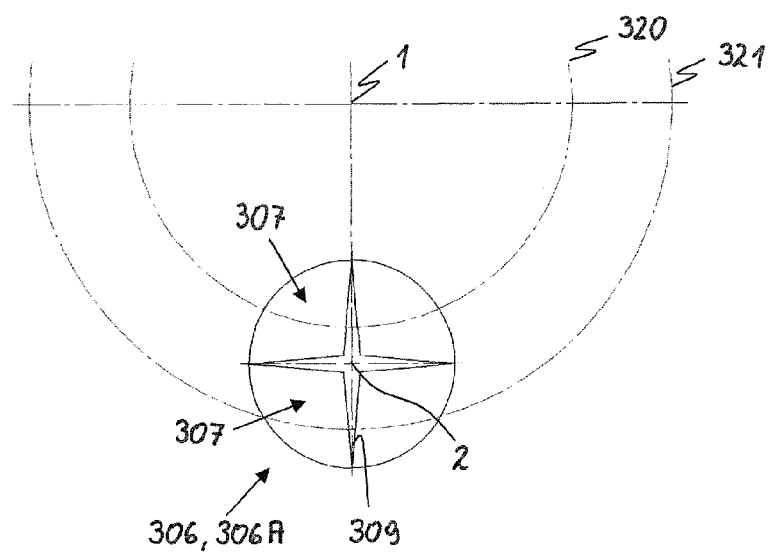
FIG. 11 shows the arrangement of the carrier unit of the drive device or of the eccentric gear unit of FIG. 9 relative to the orbits on which the eccentric pins move.

In particular it can be seen from FIG. 11 that at least two of these several eccentric pins 304, 305 can be moved on orbits 320, 321 at different distances. The two orbits 320, 321 in particular have a common center, which is preferably determined in cross-section through the output shaft 301 by the first rotational axis 1, or through which the first rotational axis 1 extends. The two orbits 320, 321 in particular have different radii from the central point or from the first rotational axis 1.

The carrier unit 306 comprises a single tappet 306A to which in particular all eccentric pins 304, 305 are assigned. The eccentric pins 304, 305 in particular engage alternately into the tappet 306A and/or contact the tappet 306A alternately. The tappet 306A in particular comprises multiple sections 307 separated from one another into which the eccentric pins 304, 305 engage. The sections 307 are designed as chambers or as recesses extending from the surface of the output shaft 302 towards the second rotational axis 2 and are separated from one another by walls or projections 309. The carrier unit 306 or tappet 306A is in particular formed as a part of the output shaft 302 or integrally with the output shaft 302. The outer diameter of the carrier unit 306 or tappet 306A is in particular, at least in the area of the walls or projections 309, substantially equal to the outer diameter of the output shaft 302.

In particular from FIG. 11 it can be seen that at least parts of the tappet 306A, in particular parts of the separated sections 307 and/or walls or projections 309 are arranged between the orbits 320, 321 on which at least two of the multiple eccentric pins 304, 305 move. Alternatively or additionally, a rotational axis 2 of the tappet 306A, which is for example identical to the second rotational axis 2 of output shaft 302, is arranged between the orbits 320, 321.

The functioning of the drive device 300 or eccentric gear unit 303 is as follows: When drive shaft 301 is rotated, then at least one eccentric pin 305 that is a first distance from the first rotational axis 1 moves on orbit 320, and at least another eccentric pin 304 that is a second, different distance from the first rotational axis 1 moves on orbit 321. Due to the rotation, the eccentric pins 304, 305 engage tappet 306A and/or make contact with it, so that tappet 306A is set into rotation by the eccentric pins 304, 305. In particular due to the offset or angled arrangement described above for said at least one eccentric pin 304 and said at least one eccentric pin 305, the eccentric pins 304, 305 come into contact with and move the tappet 306A with a time offset or at different points in time. In particular due to the arrangement described above of at least parts of the tappet 306A between the orbits 320, 321, an eccentric pin 304, 305 moves the tappet 306A in one rotational direction and the other eccentric pin 304, 305 moves the tappet 306A in the opposite rotational direction. In particular due to the different distances of eccentric pins 304, 305 from the rotational axis 1, 2, the angles of rotation through which the tappet 306A is moved in one rotational direction and in the opposite rotational direction are different. Accordingly, the tappet 306A and the output shaft 302 connected to the tappet 306A are set into an oscillating rotational motion, in which the eccentric pin 304 moves the tappet 306A in a first rotational direction through a first angle of rotation and eccentric pin 305 moves the tappet 306A in a second rotational direction opposite the first rotational direction through a second angle of rotation, which is smaller than the first angle of rotation.

FIG. 10 shows a gripping section 353 of a treatment device 350 or a hand grip element 350A, wherein the drive device 300 or the eccentric gear unit 303 is accommodated in the gripping section 353, in particular in a bend or in an angle of the gripping section 353 of a hand grip element 350A formed as a contra-angle handpiece. The output shaft 302 provided with the carrier unit 306 or the tappet 306A can be arranged either at an angle to the drive shaft 301, as shown in FIG. 10, or it can alternatively be arranged parallel to or not at an angle to drive shaft 301. In the latter case, the output shaft 302 can preferably be formed as a kind of intermediate drive located between the drive shaft 301 and another shaft oriented at an angle to the drive shaft 301, and in particular establishes an operational or motion-transmitting connection between these two shafts.

Further characteristics of the drive devices 500; 600; 700 will be described below (see FIGS. 12-15):

In addition to the eccentric gear unit 503; 603; 703 already described above, the drive device 500; 600; 700 comprises a second gear unit 531; 631; 731, so that these two gears preferably form a transmission unit 530; 630; 730 for transmitting the drive motion from the drive shaft assembly 501; 601; 701 or drive shaft 501A; 601A; 701A to the output shaft 502; 602; 702. The transmission unit 530; 630; 730 or the two gear units 503, 531; 603, 631; 703; 731 are designed in such a way that they set the output shaft 502; 602; 702 and a tool that can be connected to the output shaft 502; 602; 702 into an oscillating rotational motion with different or equal angles of rotation.

The drive device 500; 600; 700 or transmission unit 530; 630; 730 comprises a first drive-side transmission element 504; 604; 704 and a first output-side transmission element 506; 606; 706, wherein the drive-side transmission element 504; 604; 704 can be set into rotation by the drive shaft (unit) 501; 601; 701; 501A; 601A; 701A around the first rotational axis 1. The first drive-side element 504; 604; 704 is arranged concentrically to the first rotational axis 1 of drive shaft 501A; 601A; 701A. The first drive-side transmission element 504; 604; 704 and the first output-side transmission element 506; 606; 706 preferably form at least a part of the second gear unit 531.

The drive device 500; 600; 700 or transmission unit 530; 630; 730 furthermore comprises a second drive-side transmission element 505; 605; 705 and a second output-side transmission element 507; 607; 707. The second drive-side transmission element 505; 605; 705 and the second output-side transmission element 507; 607; 707 preferably form at least a part of an eccentric gear unit, in particular of eccentric gear unit 503; 603; 703. However, the eccentric can also be formed differently, for example as eccentric gear unit 204, 206 or eccentric gear unit 205, 207 in FIGS. 5-7, or as any other arbitrary eccentric gear unit.

The eccentric gear unit 503; 603; 703 comprises an eccentric element or an eccentric pin 505; 605; 705 and a receiving unit 507; 607; 707 for the eccentric element or eccentric pin 505; 605; 705. The eccentric pin 505; 605; 705 is preferably formed as a second drive-side transmission element on drive shaft 501A; 601A; 701A and receiving unit 507; 607; 707 as a second output-side transmission element on output shaft 502; 602; 702. The structure of eccentric gear units 503; 603; 703 is identical, so that the following more detailed description of eccentric gear unit 503 applies in a corresponding manner to eccentric gear unit 603; 703.

Receiving unit 507; 607; 707 of the eccentric gear unit 503; 603; 703 comprises multiple separated receiving elements 507A-C; 607A, B; 707A, B into which the eccentric pin 505; 605; 705 successively engages. The receiving unit 507; 607; 706 preferably comprises between two and five, in particular three, receiving elements 507A-C; 607A, B; 707A, B.

Receiving elements 507A-C; 607A, B; 707A, B are separated from one another by recesses 522. The recesses 522 are in particular designed in such a way that the eccentric pin 505; 605; 705 can be held in them or pass through the recesses 522. The recesses 522 are preferably arranged or designed in such way that when the eccentric pin 505; 605; 705 is held in them then the eccentric gear unit 503; 603; 703 does not establish an operational connection for the transmission of the drive movement from the drive shaft assembly 501; 601; 701 to the output shaft 502; 602; 702. Particularly preferably, during this the second gear unit 531; 631; 731 establishes an operational connection for the transmission of the drive movement from the drive shaft assembly 501; 601; 701 to the output shaft 502; 602; 702.

Each receiving element 507A-C; 607A, B; 707A, B comprises at least one groove or guide 508, in particular with multiple mutually connected groove sections 509-511 arranged at angles to one another. The groove 508 is designed to receive the eccentric element or eccentric pin 505; 605; 705. The interaction of the eccentric pin 505; 605; 705 with at least a part of the groove 508 or at least a groove section 509-511 causes a movement of the output shaft 502; 602; 702 in a rotational direction 3, 4.

Preferably said at least one groove 508 comprises at least one groove section 510 from which a first arm 509 extends in a first direction and a second arm 511 in a second direction that differs from the first direction. Preferably the groove sections 509-511 are arranged in such a way that the eccentric pin 505; 605; 705 engages in several or all groove sections 509-511.

Each receiving element 507A-C; 607A, B; 707A, B or said at least one groove 508 of each receiving element 507A-C; 607A, B; 707A, B comprises an entry opening 520 through which the eccentric pin 505; 605; 705 enters the receiving element 507A-C; 607A, B; 707A, B, and exit opening 521 through which the eccentric pin 505; 605; 705 exits the receiving element 507A-C; 607A, B; 707A, B. The entry opening 520 and exit opening 521 are preferably at a distance from one another, in particular located on opposite sides of a receiving element 507A-C; 607A, B; 707A, B.

The operational connection for the transmission of the drive movement from the drive shaft assembly 501; 601; 701 to the output shaft 502; 602; 702 between the first drive-side transmission element 504; 604; 704 and the first output-side transmission element 506; 606; 706 and/or between the second drive-side transmission element/eccentric pin 505; 605; 705 and the second output-side transmission element/receiving unit 507; 607; 707 exists only during a part of a complete rotation of a drive-side transmission element 504, 505; 604, 605; 704, 705 around the first rotational axis 1 of the drive shaft assembly 501; 601; 701.

Transmission unit 530; 630; 730 is preferably designed in such a way that it is possible to establish an operational connection alternately or in a temporally offset manner between the first drive-side and output-side transmission element 504, 506; 604, 606; 704, 706 (of the second gear unit 531; 631; 731) and between the second drive-side and output-side transmission element 505, 507; 605, 607; 705, 707 (of the eccentric gear unit 503; 603; 703) for the transmission of the drive movement from the drive shaft assembly 501; 601, 701 to the output shaft 502; 602; 702.

The existence of the operational connection between the second drive-side and output-side transmission element 505, 507; 605, 607; 705, 707 (of eccentric gear unit 503; 603; 703) only during a part of a complete rotation of a drive-side transmission element 504, 505; 604, 605; 704, 705 is achieved by the alternating receiving of the second drive-side transmission element/eccentric pin 505; 605; 705 in recesses 522 and in the second output-side transmission element/receiving unit 507; 607; 707, as already described above.

The existence of the operational connection between the first drive-side and output-side transmission element 504, 506; 604, 606; 704, 706 (of the second gear unit 531; 631; 731) only during a part of a complete rotation of a drive-side transmission element 504, 505; 604, 605; 704, 705 is achieved by the following characteristic: at least a first drive-side transmission element 504; 604; 704, or a first output-side transmission element 506; 606; 706 comprises a first section 504A; 606A; 704A, that, for the transmission of the drive movement from drive shaft assembly 501; 601; 701 to the output shaft 502; 602; 702, can be operationally connected to the corresponding drive-side transmission element 604 or output-side transmission element 506; 706, and a second section 504B; 606B; 704B in which the operational connection between the drive-side transmission element 504; 604; 704 and the output-side transmission element 506; 606; 706 is released, so that no transmission of the drive shaft movement from the drive shaft assembly 501; 601; 701 to the output shaft 502; 602; 702 takes place. The first section 504A; 606A; 704A preferably projects over the second section 504B; 606B; 704B in the direction of the drive-side or output-side transmission element 504, 506; 604, 606; 704, 706 with which the first section 504A; 606A; 704A enters into the operational connection.

Figure 13:
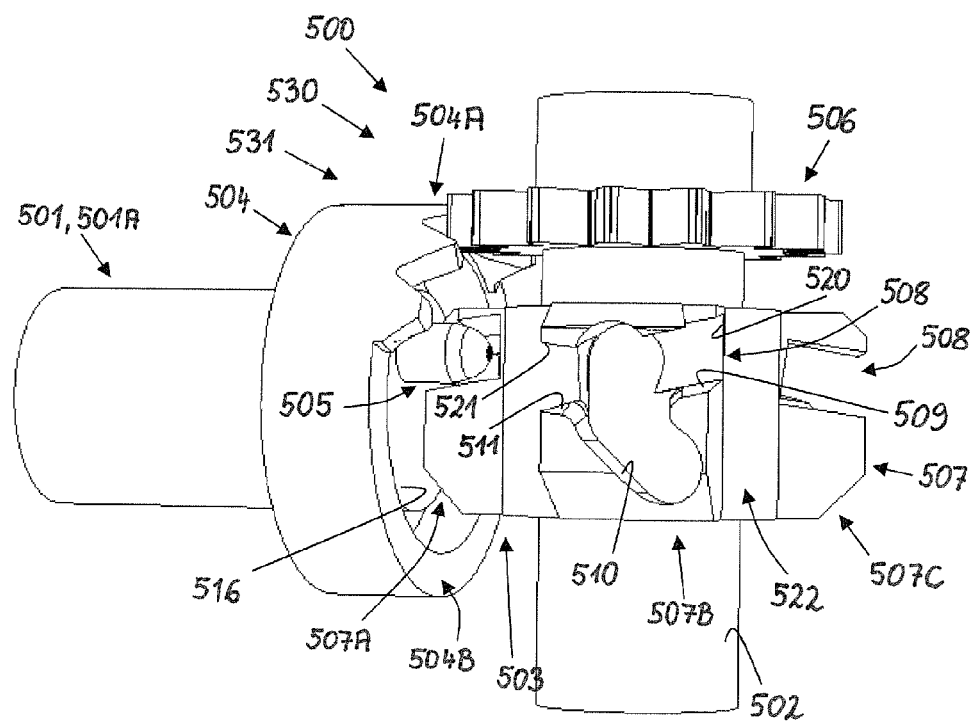
FIG. 13 shows the transmission unit of FIG. 12 in an enlarged representation.

As can be seen from FIGS. 13-15, the second gear unit 531; 631; 731 comprises different gear types depending on the embodiment: the second gear unit 531 in FIG. 13 comprises a positive gear unit, in particular a gearwheel gear unit. The gearwheel gear unit comprises a gearwheel, which for example forms the first output-side transmission element 506, and an element that has teeth along an arc or partly around its circumference, which forms for example the first drive-side transmission element 504. Accordingly, the first section 504A comprises the toothed area of the drive-side element 504 and the second section 504B a non-toothed area, in particular an area designed as a flat surface, of the first drive-side element 504.

The second gear unit 631 in FIG. 14 comprises a force-fitting or friction-fitting gear unit. The friction-fitting gear unit comprises a first friction element, which for example forms the first drive-side transmission element 604, having a friction-fitting surface 623, and a second friction element which for example forms the first output-side transmission element 606. The first section 606A comprises at least one friction-fitting surface 624 and the second section 606B comprises for example a flat surface 625 on the first output-side transmission element 606. The friction-fitting surface 624 of the first section 606A projects over the second section 606B, in particular in the direction of the first drive-side transmission element 604, so that the friction-fitting surface 624 can be brought into contact with the friction-fitting surface 623 of the first drive-side transmission element 604. The friction-fitting surface 623 is preferably located on a front face or on a side of the first drive-side transmission element 604 that is facing the friction-fitting surface 624. The friction-fitting surface 624 is preferably located on a circumferential side or on a side of the first drive-side transmission element 606 that is facing the friction-fitting surface 623.

The second gear unit 731 in FIG. 15 comprises a magnetic gear. The magnetic gear unit comprises a first drive-side transmission element 704 having at least a first magnetic area, formed for example by one or more first magnetic elements, and a first output-side transmission element 706 with at least a second magnetic area, formed for example by one or more second magnetic elements. The first section 704A comprises said at least one magnetic area of the first drive-side transmission element 704. The second section 704B comprises for example a non-magnetic or (in comparison with the magnetic area 704A) a magnetically weaker area. The magnetic area of the first section 704A projects over the second section 704B, in particular in the direction of the first output-side transmission element 706. The magnetic area 704A is preferably located on a front face or on a side of the first drive-side transmission element 704 facing the second magnetic area of the first output-side transmission element 706. The second magnetic area of the first drive-side transmission element 706 is preferably located on a circumferential side or on a side of the first output-side transmission element 706 facing the magnetic area 704A.

Figure 16:
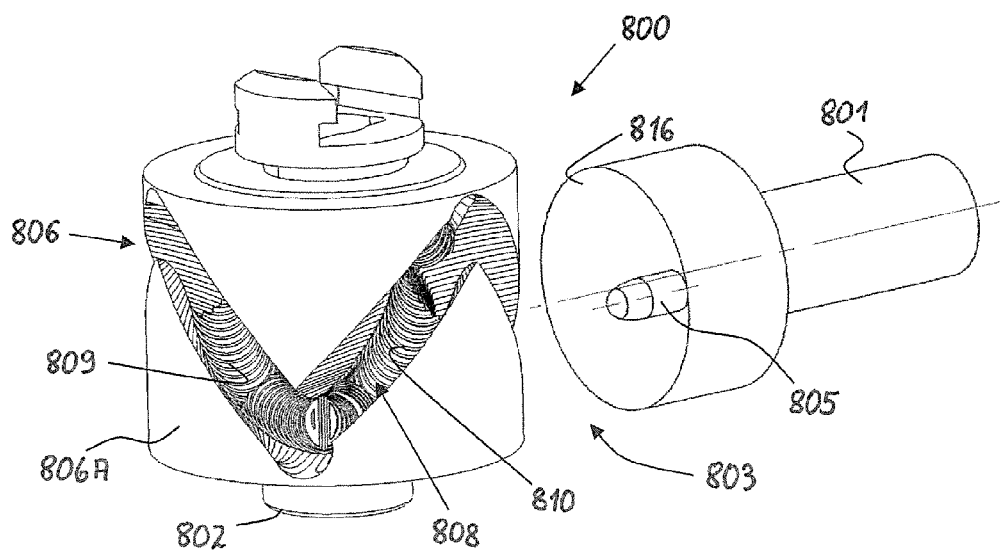
FIG. 16 shows a seventh embodiment of a drive device or an eccentric gear unit that is designed to set the tool into an oscillating rotational movement.

The drive device 800 in FIG. 16 is a variation of the drive device 100 in FIGS. 1-4. Accordingly, the drive device 800 comprises: A drive shaft 801 rotating about a first rotational axis 1 which is designed for the transmission of a drive movement, in particular in the form of a unidirectional rotational movement, an output shaft 802 that can be set into an oscillating rotational movement and that can rotate about a second rotational axis 2, and an eccentric gear unit 803 that connects the drive shaft 801 and the output shaft 802, wherein the eccentric gear unit 803 comprises at least one eccentric pin 805 and at least one receiving unit or carrier unit 806 for the eccentric pin 805, which co-operate or are designed in such a way that the output shaft 802 and a tool that can be connected to the output shaft 802 can be placed into the oscillating rotational movement.

The drive device 800 thus comprises only one gear unit, in particular only a single eccentric gear unit 803, in order to convert the drive movement provided by the drive shaft 801, in particular the unidirectional rotational movement, into the oscillating rotational movement.

Regarding further preferred characteristics of drive device 800, we refer to the description above of the drive devices with only one gear unit, in particular only a single eccentric gear unit, for the conversion of the unidirectional rotational movement provided by the drive shaft into the oscillating rotational movement, in particular to the description related to drive device 100 and/or FIGS. 1-4. The characteristics described there are applicable in a corresponding manner to drive device 800 and can be combined with it.

A significant difference between drive device 100 and drive device 800 consists in the configuration or form of receiving unit 806 or track or groove 808 for the eccentric pin 805. The receiving unit 806 for the eccentric pin 805 is preferably provided on a substantially cylindrical surface 806 surrounding the first rotational axis 1 or the second rotational axis 2, or it is part of a cylindrical body 806A that surrounds the second rotational axis 2. The holding or carrier unit 806 for the eccentric pin 805 preferably comprises a self-contained (or endless) track or guide 80 that surrounds the first rotational axis 1 or the second rotational axis 2. Particularly preferably, the receiving unit 806, in particular the track or guide 808, extends substantially in a sinuous or curved manner around the first rotational axis 1 or the second rotational axis 2, in particular on the substantially cylindrical surface 806A surrounding the first rotational axis 1 or the second rotational axis 2.

The receiving unit 806 or track 808 for the eccentric pin 805 comprises multiple sections 809, 810 connected with each other and arranged at angles to one another. The sections 809, 810 preferably run in a V-shape or zig-zag arrangement on the cylindrical surface of the body 806A, in particular alternatingly a section 809 descends in the direction of the tool receptacle opening 154; 254; 554 and an adjoining section 810 ascends away from the tool receptacle opening 154; 254; 554.

The receiving or carrier unit 806 or groove 808 for the eccentric pin 805 preferably comprises at least a first portion that causes a rotation of output shaft 2 in the first rotational direction, and a second portion that causes a rotation of the output shaft 2 in the second rotational direction. The first portion and/or second portion can optionally each be substantially identical with one of the sections 809, 810 arranged at an angle to one another, or can comprise only a part of a section 809, 810, or at least a part of each of the two sections 809, 810 arranged at an angle to one another. The first portion and the second portion preferably have different lengths. In particular, the portion that causes a rotational movement of the output shaft 802 in the preferred direction has a longer length than the portion that causes a rotational movement of the output shaft 802 in the direction opposite the preferred direction.

The drive devices 400; 400' shown in FIGS. 17-22 for a medical, in particular dental or surgical, tool are designed to set a tool into an oscillating rotational movement, wherein the oscillating rotational movement comprises an alternating rotation of the tool by a first angle in a first rotational direction and by a second angle in a second rotational direction substantially opposed to the first rotational direction, wherein the first and the second angles have different values, so that, during multiple sequential rotations in the first and in the second rotational direction the tool experiences in total a rotational movement in a preferred direction. The tools that can be connected to drive devices 400; 400' are preferably endodontic tools, for example files, in particular tools for the processing of the root canal.

The drive devices 400; 400' comprise a drive shaft 401 rotating about a first rotational axis 1, which is designed to transmit a unidirectional rotational movement, an output shaft 402 that can be set into an oscillating rotational movement and that can rotate about a second rotational axis 2, and a gear unit 403, 403' that connects the drive shaft 401 and the output shaft 402. The drive shaft 401 can be or is connected to a drive unit, for example a motor, in particular an electric motor. The drive shaft 401 is preferably rotatably supported by a bearing, in particular in a treatment device 450 or in a hand grip element 450A. At least parts of the drive device 400, 400' are held or supported in a bearing sleeve 416.

The gear unit 403, 403' comprises an eccentric pin 404 provided on an end surface or a flange 417 of drive shaft 401 so that it is connected to drive shaft 401, wherein the end surface 417 in particular is facing the output shaft 402. The eccentric pin 401 is arranged eccentrically to the first rotational axis 1 of the drive shaft 401 and can be set into rotation by the drive shaft 401. The at least one eccentric pin 404 is preferably located on or near the outer edge of the end surface 417. The end surface 417 preferably has a greater outer diameter than the drive shaft 401.

The gear unit 403, 403' furthermore comprises multiple (at least three) gearwheels 407, 408, 409 interlocking with each other and, as shown in FIG. 17, additionally a fourth gearwheel 410 as well. The gearwheels 407-410 are operationally connected to eccentric pin 404, so that the rotational movement of the drive shaft 401 can be transmitted to the gearwheels 407-410 and in particular from them to the output shaft 402.

Figure 19:
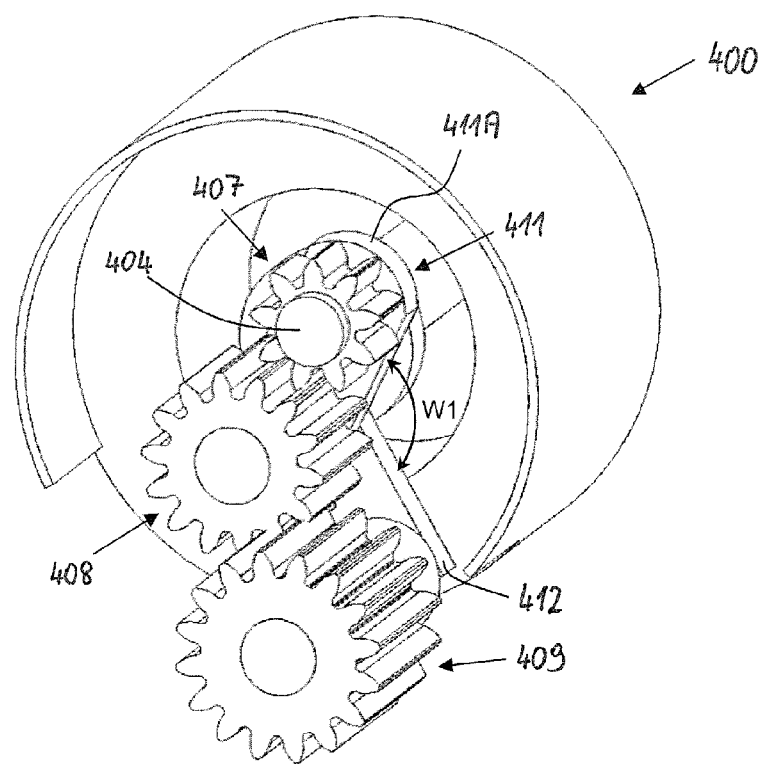
FIGS. 19-21 show different positions that the gearwheels and carrier elements may take during operation of the drive device in FIG. 18.

Drive device 400, 400' or the gear unit 403, 403' furthermore comprise a first carrier element 411 and a second carrier element 412 that form or enclose an angle W1 (see FIG. 19). The first carrier element 411 and the second carrier element 412 can be moved relative to one another in such a way that the angle W1 formed by the two carrier elements 411, 412 is variable. The two carrier elements 411, 412 are connected to one another by shaft 413 in such a way that they can rotate relative to one another. The carrier element 411 is connected movably with eccentric pin 404, or fastened to the eccentric pin 404 movably, in particular rotating.

A first gearwheel 407 is connected to eccentric pin 404 or fastened to it in a non-rotating manner. A second gearwheel 408 is engaged with the first gearwheel 407 and is provided on shaft 413 which connects the two carrier elements 411, 412. The first gearwheel 407 and the second gearwheel 408 are assigned to the first carrier element 411 or connected to it, and in particular designed to rotate relative to the first carrier element 411. A third gearwheel 409 is engaged with the second gearwheel 408. The third gearwheel 409 is assigned to the second carrier element 412 or connected to it, and designed to rotate relative to the second carrier element 412.

As shown in FIG. 18, the third gearwheel 409 is connected to the output shaft 402 in a non-rotating manner. Alternatively, as shown in FIG. 17, a fourth gearwheel 410 can be provided that engages with the third gearwheel 409 and is connected to the output shaft 402 in a non-rotating manner. The fourth gearwheel 410 and/or the output shaft 402 connected to it are arranged at an angle to gear unit 403 or to the drive shaft 401 or to the first rotational axis 1, so that the gear unit 403 can in particular be inserted into a curved section of a medical, in particular dental or surgical, treatment device 450, preferably of a medical, in particular dental or surgical, hand grip element 450A.

The two carrier elements 411, 412 form a joint or a jointed connection 418 that can move on shaft 413 and is supported rotatably on a pivot or a rotational axis. According to FIG. 18, the pivot or rotational axis is located in the second rotational axis 2 of the output shaft 402 or is identical to the second rotational axis 2. According to FIG. 17, the third gearwheel 409 is connected through a shaft 419 to the second carrier element 412, wherein the pivot of the join 418 lies in the rotational axis of shaft 419, or the rotational axis of the joint 418 is identical to the rotational axis of shaft 419.

The joint 418 can be moved during operation of the gear unit 403, 403' in such a way that the first gearwheel 407 and the second gearwheel 408 can slide in planes that are oriented substantially at right angles to the drive shaft 401 and/or to the output shaft 402 and/or essentially parallel to end surface 417. In particular the first gearwheel 407 connected to eccentric pin 404 in a non-rotating manner can slide relative to the second rotational axis 2 of output shaft 402 in such a way that the distance between the first gearwheel 407 and the second rotational axis 2 is variable. The second gear wheel 408 is in particular capable of sliding relative to the first rotational axis 1 of drive shaft 401 in such a way that the distance between the second gearwheel 408 and the first rotational axis 1 is variable. Due to the joint 418, the first gearwheel 407 can also slide relative to the third gearwheel 409 in such a way that the distance between these two gearwheels 407, 409 is variable.

In contrast, the distance from the third gearwheel 409 and, if present, the fourth gearwheel 410 to the first rotational axis 1 and to the second rotational axis 2 is constant. The third gearwheel 409 is in particular arranged concentrically to the rotational axis of joint 418.

As can particularly be seen in FIG. 18, the two gearwheels 407, 409, the distance between which is variable, are arranged axially offset from one another (relative to the first and/or second rotational axis 1, 2) in such a way that, during operation of drive device 400, 400' and at least during a temporally limited duration, the two gearwheels 407, 409 can move axially (relative to the first and/or second rotational axis 1, 2) into a position in which they at least partly overlap one another. To do this, there is a free space 415 provided between the third gearwheel 409 and the carrier element 412, so that during operation of the drive device 400, 400' and at least during a temporally limited duration, the first gearwheel 407 and/or the carrier element 411, on which the first gearwheel 407 is located, can move at least partly into the free space 415. To provide the free space 415, as shown in FIG. 17, the shaft 419 has a sufficiently long design so that the third gearwheel 409 is sufficiently distant from carrier element 412 in order to receive the first gearwheel 407 and/or the carrier element 411 between the third gearwheel 409 and the carrier element 412. According to FIG. 18, on carrier element 412 there is a projection or angled element 412A to which the third gearwheel 409 is connected. The projection 412A separates the third gearwheel 409 from the carrier element 412, thus creating free space 415.

Figure 23:
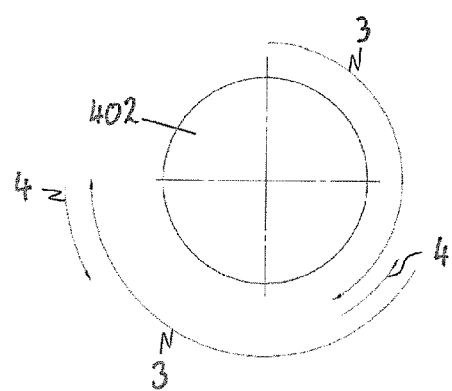
FIG. 23 shows a schematic example of an oscillating rotational movement as it can be generated by a drive device that converts a unidirectional rotational movement into an oscillating rotational movement.

The oscillating rotational movement generated by drive device 400; 400' or by gear unit 403 and transmitted to the output shaft 402 and/or a tool connected to it is shown in FIG. 23. The output shaft 402 or the tool rotate alternately in a first rotational direction 3 (for example in a preferred or working direction in which the tool removes material, preferably tissue, in particular tissue of a dental root canal) by a first angle of rotation and in a second rotational direction 4 (opposite the preferred or working direction, for example called the return direction, in which in particular the removed material is carried away by the tool), which is substantially opposite the first rotational direction 3, by a second angle of rotation, wherein the first and the second angles of rotation have different values. According to the embodiment shown, for example, the angle of rotation in the first rotational direction 3 is about 150° and the angle of rotation in the second rotational direction 4 is about 30°. Clearly, other arbitrary values are possible for the angle of rotation, as long as the angles of rotation differ, for example by about 45° and 20°, 180° and 90°, 270° and 90°, etc. The rotational directions shown in FIG. 23 are also an example only, so it is just as possible to reverse the rotational directions of the two rotational movements 3, 4 shown in FIG. 23, that is, rotational direction 3 would then be counterclockwise and rotational direction 4 clockwise.

The frequency of the oscillation movement of the drive shaft 402 or the tool, for example, lies in a range of about 3-50 Hertz, preferably in the range from about 5-20 Hertz, in particular about 10 Hertz.

Figure 20:
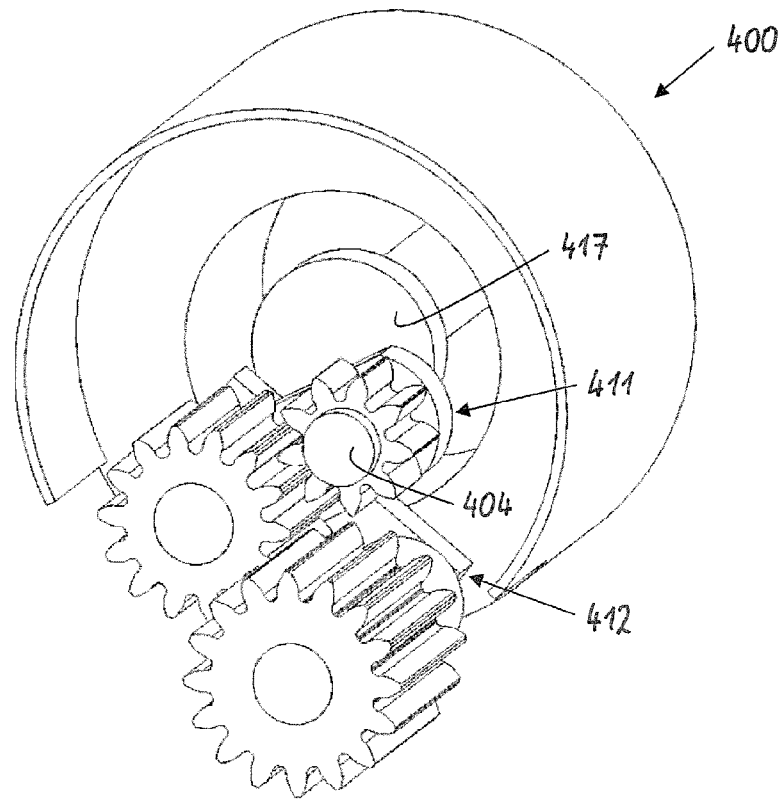
Figure 21:
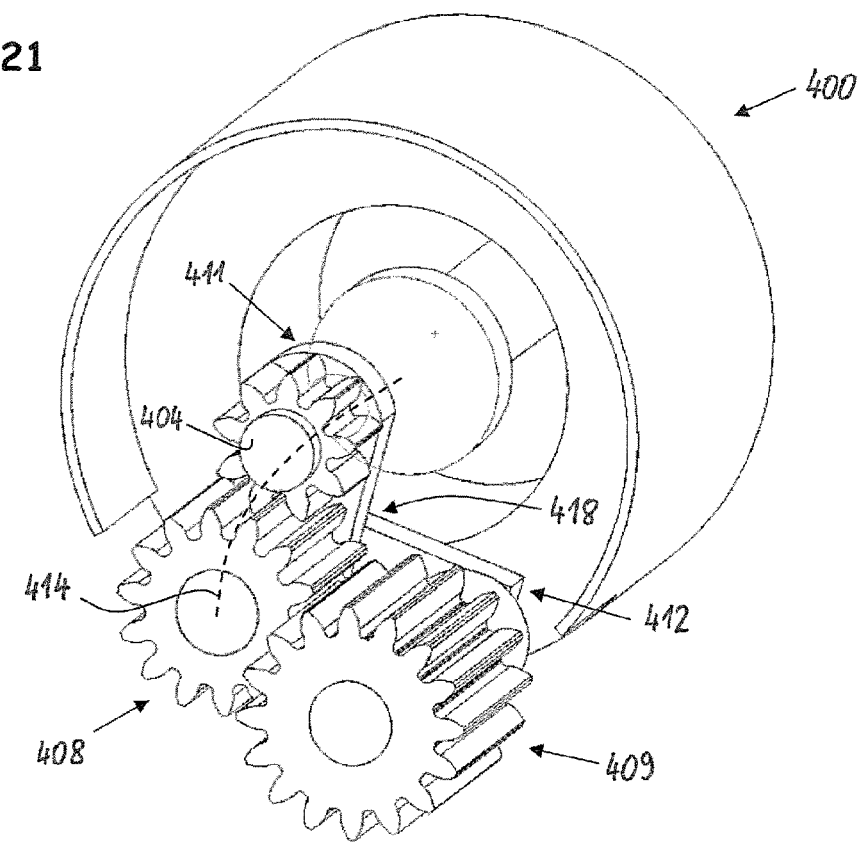

The functional principle of the drive device 400 (and drive device 400' in a corresponding manner) will be explained on the basis of FIGS. 19-21: The eccentric pin 404 moves in a circular manner on a track around the first rotational axis 1, which is determined by the position of the eccentric pin 404 on the end surface 417. In a corresponding manner, the first gearwheel 407 fastened in a non-rotating manner on eccentric pin 404 moves along an orbit around the first rotational axis 1 (without relative motion with respect to the eccentric pin 404). Since one end 411A of the carrier element 411 is also provided on eccentric pin 404 or fastened there in a rotating manner, the carrier element 411, in particular end 441A, follows the movement of the eccentric element and moves on a self-contained track.

The (unidirectional) rotational movement transmitted by the drive shaft 401 is transmitted to the drive shaft 402 through the mutually engaged gearwheels 407-409 and optionally 410. Due to the rotation of drive shaft 401 and through the connection of end 411A of carrier element 411 to the eccentric pin 404 and the fastening of carrier element 412 to the pivot or rotational axis 2, the two carrier elements 411, 412 are moved relative to one another, in particular in such a way that that the angle W1 formed by carrier elements 411, 412 changes. The movement of carrier elements 411, 412 is in particular defined in such a way that the carrier elements 411, 412 move in a plane that is oriented substantially at right angles to the drive shaft 1 and/or output shaft 2.

The gearwheels 407, 408 provided on carrier elements 411, 412 follow the movement of the carrier elements 411, 412; in particular the second gearwheel 408 is moved in the plane mentioned above so that it can slide relative to the drive shaft 401 and/or to the first rotational axis 1 of drive shaft 401 in such a way that the distance between the second gearwheel 408 and the drive shaft 401 and/or the first rotational axis 1 is variable. In particular the second gearwheel 408 is arranged in such a way that, just as joint 418, it can move back and forth along a preferably circular arc shaped track. This circular arc shaped track 414 is shown approximately in FIG. 21. It can be seen that the circular arc shaped track 414 is arranged around the third gearwheel 409 or surrounds the third gearwheel in a circular arc, so that the second gearwheel 408 and the joint 418 are moved back and forth in the plane relative to the third gearwheel 409. Accordingly, during a temporally limited and recurring period the second gearwheel 408 and the joint 418 move relative to the third gearwheel 409 such, that the movement in the second rotational direction 4 (the return direction) is caused.

Figure 22:
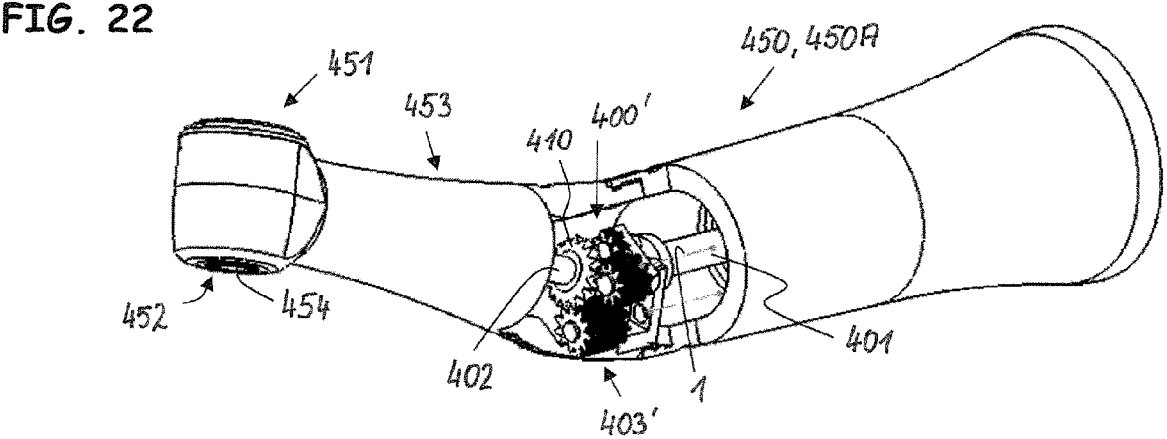
FIG. 22 shows a medical, dental or surgical treatment device with a drive device according to FIG. 18.

FIG. 22 shows the drive device 400' or the gear unit 403' in a medical, in particular a dental or surgical, treatment device 450 and/or in a medical, in particular a dental or surgical, hand grip element 450A. The drive device 400 or gear unit 403 can also be arranged in a corresponding manner in the treatment device 450 or in the hand grip element 450A. Treatment device 450 or hand grip element 450A comprise a head section 451 and an adjoining gripping section 453. In the head section 451 there is a tool-holding device 452. A tool receptacle opening 454 is provided on the side of the head section 451. The drive device 400', 400 or the gear unit 403', 403 are held in the gripping section 453, in particular in a bend or in an angle of the gripping section 453 of a hand grip element 450A designed as a contra-angle handpiece. The output shaft 402 can be arranged either at an angle to drive shaft 401, as shown in FIG. 22, or it can alternatively be arranged parallel to or not at an angle to drive shaft 401. In the latter case, output shaft 402 can preferably be formed as an intermediate drive located between the drive shaft 401 and another shaft oriented at an angle to the drive shaft 401, and in particular establishes an operational or movement-transmitting connection between these two shafts.

The invention is not limited to the embodiments described here, but instead comprises all embodiments deploying or including the basic, analogous functional principle of the invention. In particular, all the drive devices described above can be implemented not only in a hand grip element, but also in a motor, in particular in a pneumatically drive motor, in a coupling unit, or in an adapter. The motor, the coupling unit or the adapter can preferably be connected to the hand grip element in a detachable manner in such a way that the oscillating rotational motion can be transmitted via the interface between the hand grip element and the motor, the coupling unit or the adapter and by means of at least one drive shaft in the hand grip element to a tool held in the hand grip element. Furthermore, each feature of each embodiment described and illustrated here can be combined with each another.

What is claimed is:

1. A drive device for a medical, dental or surgical tool, comprising:
   a drive shaft rotatable about a first rotational axis and configured to transmit a unidirectional rotational motion,
   an output shaft that is set into an oscillating rotational motion and rotates about a second rotational axis, wherein the oscillating rotational motion comprises an alternating rotation of the output shaft by a first angle of rotation in a first rotational direction and by a second angle of rotation in a second rotational direction, substantially opposed to the first rotational direction,
   wherein the first and second angles of rotation have different values, so that, during multiple sequential rotations in the first and second rotational directions, the medical, dental or surgical tool coupleable to the output shaft cumulatively experiences a rotational movement in a preferred direction, and
   an eccentric gear unit that connects the drive shaft with the output shaft, wherein the eccentric gear unit comprises at least one eccentric gear pin and at least one carrier unit or receiving unit for said at least one eccentric pin, which work together such that the output shaft and the medical, dental or surgical tool can be set into the oscillating rotational motion, wherein
   the carrier unit or receiving unit for the at least one eccentric pin comprises a single, continuous track surrounding the second rotational axis and accommodating the eccentric pin, and wherein the single, continuous track comprises at least a first section and an adjacent second section that extend in different directions and form an angle therebetween so that when the drive device is actuated, the at least one eccentric pin is received in the first section or the second section and then in the other of the first section or the second section, thereby setting the dental or surgical tool into the oscillating rotational motion.

2. The drive device according to claim 1, wherein the eccentric gear unit comprises a plurality of eccentric pins, wherein at least two of these eccentric pins are at different distances from the first rotational axis of the drive shaft and/or from the second rotational axis of the output shaft.

3. The drive device according to claim 1, wherein the carrier unit or receiving unit comprises a tappet, with which the at least one eccentric pin alternately engage and/or which it is alternately in contact with.

4. The drive device according to claim 3, wherein the at least one eccentric pin comprises a plurality of eccentric pins which are arranged in such a way that eccentric pins that engage with and/or come into contact with the tappet consecutively move the tappet in opposite rotational directions and/or through different angles of rotations.

5. The drive device according to claim 1, wherein one of the first section or the second section is configured to cause the output shaft to rotate in the first rotational direction, and the other of the first section or second section is configured to cause the output shaft to rotate in the second rotational direction.

6. The drive device according to claim 5, wherein the at least one first section and the at least one second section are of different lengths.

7. The drive device according to claim 1, wherein the eccentric gear unit comprises a first eccentric pin assigned to a first receiving unit and a second eccentric pin assigned to a second receiving unit.

8. The drive device according to claim 7, wherein the eccentric gear unit is configured such that while the first eccentric pin engages the first receiving unit to cause the output shaft to rotate, the second eccentric pin is positioned not to cause the output shaft to rotate.

9. The drive device according to claim 1, wherein the at least one eccentric gear pin rotates in the unidirectional rotational motion about the first rotational axis in unison with the drive shaft.

10. The drive device according to claim 1, wherein the track surrounding the second rotational axis comprises an undulating shape.

11. The drive device according to claim 1, wherein the track comprises a groove.

12. The drive device according to claim 1, wherein the drive device comprises a plurality of first sections and a plurality of second sections which are arranged in alternation, wherein the at least one eccentric gear pin passes successively through one of the first sections and one of the second sections.

13. The drive device according to claim 1, wherein the eccentric gear unit is configured such that it converts the unidirectional rotational motion provided by the drive shaft into the oscillating rotational motion exclusively or without another gear unit.

14. A medical, dental or surgical treatment device, having a drive device comprising:
   a drive shaft rotatable about a first rotational axis and configured to transmit a unidirectional rotational motion,
   an output shaft that is set into an oscillating rotational motion and rotates about a second rotational axis, wherein the oscillating rotational motion comprises an alternating rotation of the output shaft by a first angle of rotation in a first rotational direction and by a second angle of rotation in a second rotational direction, substantially opposed to the first rotational direction,
   wherein the first and second angles of rotation have different values, so that, during multiple sequential rotations in the first and second rotational directions, a tool coupleable with the output shaft cumulatively experiences a rotational movement in a preferred direction, and
   an eccentric gear unit that connects the drive shaft with the output shaft, wherein the eccentric gear unit comprises at least one eccentric gear pin and at least one carrier unit or receiving unit for said at least one eccentric pin, which work together such that the output shaft and the tool can be set into the oscillating rotational motion, wherein
   the carrier unit or receiving unit for the at least one eccentric pin comprises a track which circumferentially surrounds the output shaft, and wherein
   the track comprises at least a first section and an adjacent second section that extend in different directions and form an angle between therebetween so that when the drive device is actuated, the at least one eccentric pin is received in one of the first section or the second section and then in the other of the first section or the second section, thereby setting the dental or surgical tool into the oscillating rotational motion.

15. The medical, dental or surgical treatment device according to claim 14, further comprising a head section with a tool-holding device for the tool, wherein at least a part of the tool-holding device is located on the output shaft.

16. The medical, dental or surgical treatment device according to claim 14, wherein one of the first section or the second section is configured to cause the output shaft to rotate in the first rotational direction, and the other of the first section or the second section is configured to cause the output shaft to rotate in the second rotational direction.

17. A medical, dental or surgical treatment device, having a head section with a tool-holding device for a tool and a drive device, the drive device comprising:
   a drive shaft rotatable about a first rotational axis and configured to transmit a unidirectional rotational motion,
   an output shaft holding at least a portion of the tool-holding device, wherein the output shaft is set into an oscillating rotational motion and rotates about a second rotational axis, wherein the oscillating rotational motion comprises an alternating rotation of the output shaft by a first angle of rotation in a first rotational direction and by a second angle of rotation in a second rotational direction, substantially opposed to the first rotational direction,
   wherein the first and second angles of rotation have different values, so that, during multiple sequential rotations in the first and second rotational directions, a tool coupleable with the output shaft cumulatively experiences a rotational movement in a preferred direction, and
   an eccentric gear unit that connects the drive shaft with the output shaft, wherein the eccentric gear unit comprises at least one eccentric gear pin and at least one carrier unit or receiving unit for said at least one eccentric pin, which work together such that the output shaft and the tool can be set into the oscillating rotational motion, wherein
   the carrier unit or receiving unit for the eccentric pin comprises a track which circumferentially surrounds the output shaft and the portion of the tool-holding device held by the output shaft.

18. The drive device according to claim 17, wherein the track comprises a groove which surrounds the output shaft and the portion of the tool-holding device held by the output shaft in an undulating manner.

19. The drive device according to claim 17, wherein the track comprises a plurality of sections that are arranged at angles to one another.

20. The drive device according to claim 19, wherein the plurality of sections comprises at least one first section configured to cause the output shaft to rotate in the first rotational direction, and at least one second section configured to cause the output shaft to rotate in the second rotational direction.

* * * * *